US008071152B2

(12) United States Patent
Etzel et al.

(10) Patent No.: US 8,071,152 B2
(45) Date of Patent: *Dec. 6, 2011

(54) METHODS INVOLVING WHEY PROTEIN ISOLATES

(75) Inventors: Mark R. Etzel, Madison, WI (US); Thomas R. Helm, Oshkosh, WI (US); Harit K. Vyas, Fond du Lac, WI (US)

(73) Assignees: Wisconsin Alumni Research Foundation, Madison, WI (US); Grande Cheese Company, Brownsville, WI (US)

( * ) Notice: Subject to any disclaimer, the term of this patent is extended or adjusted under 35 U.S.C. 154(b) by 314 days.

This patent is subject to a terminal disclaimer.

(21) Appl. No.: 12/112,607

(22) Filed: Apr. 30, 2008

(65) Prior Publication Data

US 2009/0068326 A1    Mar. 12, 2009

Related U.S. Application Data

(63) Continuation of application No. 11/123,960, filed on May 6, 2005, now Pat. No. 7,378,123.

(60) Provisional application No. 60/569,078, filed on May 7, 2004.

(51) Int. Cl.
*A23C 9/146* (2006.01)
(52) U.S. Cl. ........ 426/656; 426/583; 426/491; 426/495; 426/271
(58) Field of Classification Search ................... 426/656, 426/583, 491, 495
See application file for complete search history.

(56) References Cited

U.S. PATENT DOCUMENTS

| | | | | |
|---|---|---|---|---|
| 4,834,994 | A | 5/1989 | Kuwata et al. | 426/271 |
| 5,756,680 | A * | 5/1998 | Ahmed et al. | 530/366 |
| 5,851,578 | A | 12/1998 | Gandhi | 426/590 |
| 5,968,586 | A | 10/1999 | Etzel | 426/657 |
| 5,986,063 | A | 11/1999 | Etzel | 530/366 |
| 6,528,622 | B1 | 3/2003 | Ayers et al. | 530/364 |
| 6,592,905 | B1 | 7/2003 | Ayers et al. | 424/535 |
| 7,378,123 | B2 | 5/2008 | Etzel et al. | 426/656 |
| 2005/0092684 | A1 | 5/2005 | Keech et al. | 210/645 |

FOREIGN PATENT DOCUMENTS

| | | |
|---|---|---|
| EP | 0 282 200 | 9/1988 |
| EP | 0282200 | * 9/1988 |
| JP | 02-104246 | 4/1990 |
| JP | 04-211100 | 8/1992 |
| JP | 05-202098 | 8/1993 |
| JP | 05-344864 | 12/1993 |

OTHER PUBLICATIONS

CRC Handbook of Chemistry and Physics, 26$^{th}$ Edition, 1954, p. 3 1623.*
Japanese Office Action, issued in Japanese Application No. 2007-511695, mail date Nov. 30, 2009 (English Translation).
"Determination of Turbidity," found on the World Wide Web at http://chemie.uni-lueneburg.de/wtw/turb_e.pdf, as early as May 6, 2005.
Beynon and Easterby, "Buffer solutions," Taylor and Francis, 1999, http://www.taylorandfrancis.co.uk/shopping_cart/products/product_detail.asp?sku=&isbn=0199634424&parent_id=&pc=/shopping_cart/search/search.asp?search=Buffer%20Solutions, Jun. 19, 2006.
Damodaran, in: *Food Chemistry*, Fennema (Ed.), Marcel Dekker Inc., NY, 321-430, 1996.
Etzel, "Manufacture and use of dairy protein fractions," *J. Nutr.*, 134:996S-1002S, 2004.
Etzel, "Protein Separation by Ion Exchange in Columns," International Whey Conference (2$^{nd}$ 1997; Chicago, IL Oct. 27-29, 1997.
Etzel, in: *Proceedings of Dry Milk and Whey Technology Forum*: Dairy Management Inc., 44-60, 1998.
Hambling et al., In *Advanced Dairy Chemistry*, vol. 1 Proteins, Fox (Ed.), Blackie Academic & Professional, NY, 141-190, 1992.
Office Action issued in U.S. Appl. No. 11/123,960, mailed Aug. 23, 2007.
Office Action issued in U.S. Appl. No. 11/123,960, mailed Aug. 8, 2006.
Office Action issued in U.S. Appl. No. 11/123,960, mailed Dec. 1, 2005.
Office Action issued in U.S. Appl. No. 11/123,960, mailed Feb. 22, 2007.
Office Action issued in U.S. Appl. No. 11/123,960, mailed Mar. 23, 2006.
Zhu and Damodaran, "Heat-Induced conformational changes in whey protein isolate and its relation to foaming properties," *J. Agric. Food Chem.*, 42:846-855, 1994.
Zumdahl, In: *Chemistry*: Third Edition, D.C. Heath and Company, MA, 1993.
Office Action in Ex Parte Reexamination, issued in U.S. Appl. No. 00/010,297, mailed May 14, 2009.
Order Granting of Ex Parte Reexamination, issued in U.S. Appl. No. 00/010,297, mailed Nov. 26, 2008.
Request for Reexamination, U.S. Patent No. 7,378,123—Methods Involving Whey Proteins Isolates, filed Sep. 30, 2008.
CRC Handbook, 36$^{th}$ Edition, p. 1623, 1954.
Tetra Pak Dairy Processing Handbook, pp. 344-345, 1995.

* cited by examiner

*Primary Examiner* — Anthony Weier
(74) *Attorney, Agent, or Firm* — Fulbright & Jaworski

(57) ABSTRACT

The present invention concerns methods and compositions that involve whey protein isolates. Methods of the invention include purification processes for preparing whey proteins that are substantially nondenatured across a range of pH, including their isoelectric points. As such, they have low turbidity in solution across a wide range of pH values. Whey protein isolates can be integrated into compositions and solutions that have nutritional, pharmaceutical, and other applications.

28 Claims, 6 Drawing Sheets

FIG. 1A-B
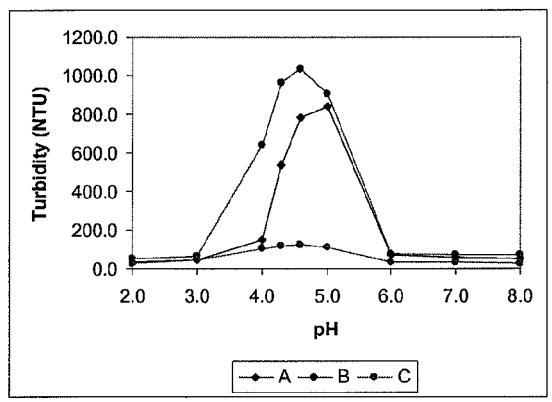
FIG. 1A
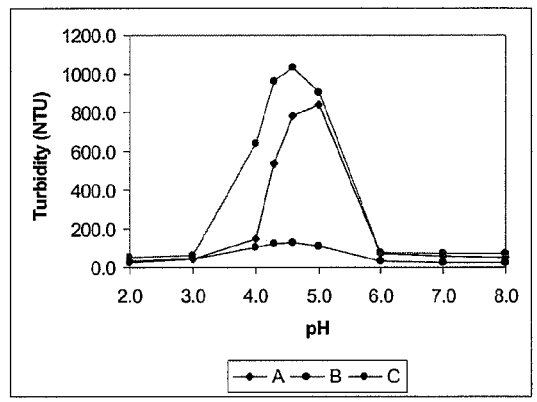
FIG. 1B
FIG. 2
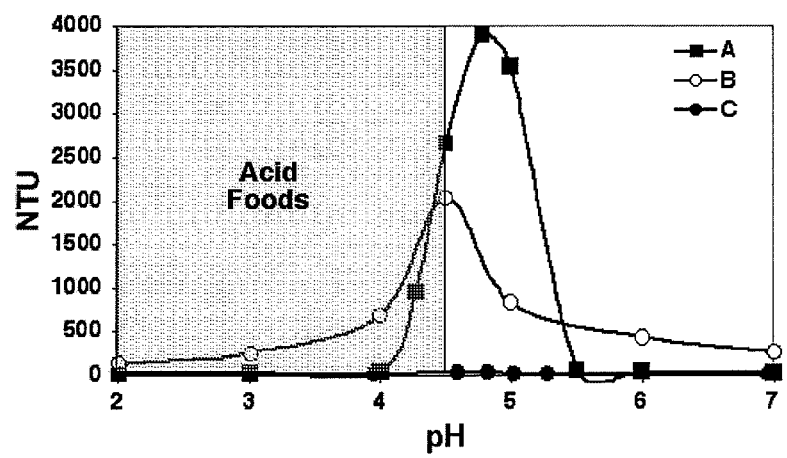

METHODS INVOLVING WHEY PROTEIN ISOLATES

RELATED U.S. APPLICATION DATA

This application is a continuation application of U.S. patent application Ser. No. 11/123,960 filed on May 6, 2005, now U.S. Pat. No. 7,378,123 which claims priority to U.S. Patent Application Ser. No. 60/569,078, filed on May 7, 2004, each of which are hereby incorporated by reference in their entirety.

BACKGROUND OF THE INVENTION

1. Field of the Invention

The present invention relates generally to the field of protein chemistry. More particularly, it provides a process of isolating whey proteins. The invention further relates to methods and compositions involving a whey protein isolate that has low turbidity across a wide range of pH values.

2. Description of Related Art

One of the most superior classes of food protein is whey protein. It is known for its excellent amino acid profile, high cysteine content, rapid digestion, and interesting bioactive proteins (lactoglobulins, immunoglobulins, and lactoferrins). Nutritionally speaking, whey protein is known as a naturally complete protein because it contains all of the essential amino acids required in the daily diet. It is also one of the richest sources of branched chain amino acids (BCAAs) which play a large role in muscle protein synthesis. Moreover, some of the individual components of whey protein have been shown to prevent viral and bacterial infection and modulate immunity in animals.

Whey protein makes up one of the two major protein groups in milk, comprising approximately 20% of the total proteins in milk. Caseins account for the other protein portion in milk. In terms of nutrition, whey protein has been rated as a higher quality protein than casein. Additionally, it is more soluble than casein, making it more attractive as food additives. Compositionally, whey protein is actually made up of a mixture of different biological proteins. The majority of whey protein consists of α-lactalbumin (alpha-LB) and β-lactoglobulin (beta-LG). Present in lesser amounts can be immunoglobulin, bovine serum albumin, glycomacropeptide, lactoferrin, and lactoperoxidase.

Whey proteins can be prepared from whey, a by-product of the cheesemaking process, or by running milk through a microfilter and collecting the flow through. Using the cheesemaking process, the production of whey protein involves several steps. After fresh milk is pasteurized, the casein or "curd" is removed to make cheese. The remaining liquid is known as whey. A number of methods are used to isolate and purify whey proteins from liquid whey. These processes include selective precipitation, membrane filtration, and ion exchange chromatography. The two major commercial isolation procedures for whey proteins are ion exchange methods and microfiltration, which yield approximately 90%-95% whey proteins.

In selective precipitation, the whey is physically adjusted to promote insolubility for a particular protein. Proteins tend to aggregate and precipitate at certain pHs and temperature. For example, α-lactalbumin precipitates at a pH of 4.2 and a temperature of 65° C. In contrast, membrane filtration is essentially separating the liquid whey by molecular mass. The liquid whey is run through semi-permeable membranes to separate whey proteins from other components. Both of these processes are volume-dependent, requiring large, expensive equipment to process large volumes of liquid whey.

Purification by ion exchange chromatography can be accomplished through two different processes: selective adsorption or selective elution. In selective adsorption, a single protein is bound to the adsorbent leaving the rest of the whey to run through the exchange column. β-lactoglobulin has been isolated in this way using immobilized retinal. Alternatively, selective elution requires that all the proteins be trapped simultaneously onto an adsorbent. The proteins are washed free from contaminants, and then eluted one by one to manufacture many different purified proteins. As opposed to selective adsorption which isolates only a single protein, selective elution allows the isolation of several different proteins. In comparison to membrane filtration and selective precipitation, ion-exchange chromatography is less volume dependent because capacity depends on mass of protein recovered, not the volume of liquid processed.

Two classes of whey protein are currently in the marketplace: whey protein concentrates and whey protein isolates. Whey protein concentrates are rich in whey proteins, but also contain fat and lactose. Typically, whey protein concentrates are produced by membrane filtration. On the other hand, whey protein isolates consist primarily of whey proteins with minimal fat and lactose. Whey protein isolates usually require a more rigorous separation process such as a combination of microfiltration and ultrafiltration or ion exchange chromatography. After whey proteins are produced in the cheesemaking process from cows' milk and the curd is removed, about 12% of the solids in the remaining byproduct liquid whey is protein. It is generally understood that a whey protein isolate refers to a mixture in which at least 90% of the solids are whey proteins. A whey protein concentrate is understood as having a percentage of whey protein between the initial amount in the byproduct and a whey protein isolate.

Whey proteins in their native state are soluble and have an average isoelectric point (pI) of about 4.6. Two major whey proteins: β-lactoglobulin and α-lactalbumin make up about 90 percent of total whey proteins and have pI values of 4.4 (Etzel 1998) and 5.2 (Hambling 1997), respectively. Whey proteins are known to remain soluble at across a range of pHs. This includes solubility at their isoelectric point, making whey proteins unique in this regard (Damodaran 1996). However, if denatured, whey proteins may aggregate and form precipitates that make the solutions turbid, particularly at and near their isoelectric pH (Damodaran 1996). Exposure to harsh processing conditions is known to denature whey proteins (Damodaran 1996). Most commercial whey protein products form turbid solutions in the pH range of about 4.0 to 5.5.

Although the use of whey protein for human food has demonstrated potential, it has limitations related to the functional properties of the whey proteins, especially in their solubility and turbidity. These shortcomings have prevented whey protein from being properly utilized in the large and growing beverage marketplace. Low-protein, high-carbohydrate drinks, such as soft drinks and fruit juice, encompass nearly 80% of the beverage market. None of these products contain a significant amount of protein. A more nutritional alternative would be a high-protein, reduced sugar drink.

Whey protein isolate would provide an ideal high-quality protein additive for such a beverage. Balancing sweetness and acidity is critical in a beverage formulation. The majority of clear soft drinks are acidic (for example, Coca Cola™ has a 2.5 pH). At a very low pH, the solutions become very tart; consequently, a large quantity of sugar is needed to sweeten the drink. In a drink with high-protein and low sugar content, to achieve the desired sweetness, the target pH would preferably have to be between 3.0 and 4.6. Unfortunately, when added to liquids, whey proteins form sedimentary layers and produce turbid solutions at pHs of 4.0 to 5.5. However, at a pH below 3.0, solutions with whey protein produce clear solutions without precipitation. The problem is that reducing the sugar content of a drink requires a corresponding increase in pH. Consequently, a beverage with high whey protein content at a pH in the desired range would be cloudy and unappetizing to the average consumer. On the other hand, lowering the pH would render the drink clear, but unpalatable unless a substantial amount of sweetener is added. Thus, methods of overcoming the problem of turbid, high pH solutions containing whey protein are needed.

SUMMARY OF THE INVENTION

The present invention is based on techniques developed for preventing the denaturation of whey proteins during their isolation. By controlling the environment in which whey proteins are desorbed from a cation exchange column, denaturation is significantly reduced or prevented. Thus, the present invention concerns methods for preparing or isolating whey protein, as well as compositions and methods concerning the use of that prepared whey protein. Methods of the invention provide a whey protein isolate or whey proteins that are substantially nondenatured. As a result, the whey proteins produced by methods of the invention are soluble across a broad range of pH, including at their isoelectric points. The resulting protein can be used in a variety of ways, such as in foodstuffs, as a protein supplement, or in pharmaceutical formulations or therapeutic applications. The term "range of pHs" covers a pH range relevant to biological systems of at least three pH units; for example, a range of pH could be from about 4 to about 6 (covering the pH units of 4, 5, and 6). The term "broad range of pH" covers a range of at least four pH units; for example, a broad range of pH could be from about 3 to about 6.

Methods of the invention for preparing whey proteins involve a particular purification process that prevents the proteins from becoming denatured and aggregating during that process. In some embodiments, there are methods of obtaining a "whey protein isolate," which refers to a mixture of whey proteins comprising two or more different whey proteins, in which 90% or more of the solids in the composition is whey proteins (that is, at least 90% of the weight of all solids in the isolate can be attributed to the weight of whey protein). In certain embodiments, an isolate is about, at least about, or at most about 90, 91, 92, 93, 94, 95, 96, 97, 98, 99% or more whey protein, or any range derivable therein. In many embodiments, the isolate contains β-lactoglobulin and α-lactalbumin. In others, the isolate does not contain glycomacropeptides. It will be understood that embodiments discussed with respect to preparing whey proteins are applicable to preparing a whey protein isolate, and vice versa, unless specifically indicated as otherwise. Furthermore, other concentrations of whey proteins can be obtained using methods of this invention.

These methods involve implementing ion exchange chromatography and employing certain conditions for retrieving the whey proteins from the chromatographic support. In embodiments of the invention, methods include: a) contacting whey proteins with a cation exchange support under conditions to allow the whey proteins to be adsorbed to the support; b) flowing a desorption solution across the support wherein the desorption solution has a pH of about 7 or more; and, c) collecting the desorbed whey proteins. In particular embodiments of the invention, the elution or desorption of proteins is implemented directionally, meaning that the desorption occurs generally in one direction. Thus, in certain embodiments of the invention, a desorption solution is applied to the support and the solution is made to flow across the support to which whey proteins are desorbed. The term "flowing" is used according to its ordinary and plain meaning as referring to "cause to move along in a current," which means in a directional manner—that is, generally in one direction. It will be understood that "generally in one direction" means that the solution flows generally directly from point A to point B. It will also be understood that, in certain embodiments desorption solution flows generally from point A to point B, and not from point B to point A. The term "contacting" is used according to its ordinary and plain meaning to refer to the "bringing together" or "placing in close proximity." The term "applying" is used according to its ordinary and plain meaning, and it includes "placing" and "adding."

In some embodiments of the invention, methods of preparing whey protein concern producing a whey protein isolate that has a relatively low turbidity compared to commercial whey protein isolates and this relatively low turbidity is preserved across a range of pH values, including at its isoelectric point. Thus, methods of the invention allow for the preparation of a whey protein isolate (about 25 g/L) that has a turbidity of about, at least about, or at most about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800 Nephelos Turbidity Units (NTU), or any range derivable therein, in a solution having a pH of about, at least about, or at most about, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0 or more, or across or within any range derivable therein. In certain embodiments, isolated whey proteins (about 25 g/L) have a turbidity below about 400 NTU across a pH range between about 2 and about 8, or a turbidity below about 200 NTU across a pH range between about 2 and about 8, or a turbidity below about 50 NTU across a pH range between about 2 and about 8. In other embodiments, a solution containing isolated whey proteins at a concentration of about 25 g/L has a turbidity below about 200 NTU across a pH range of about 4 to about 6 or a turbidity below about 50 NTU across a pH range of about 4 to about 6. It will be understood that the term "low turbidity" refers to whey proteins whose physical characteristics are such that they have an NTU of 400 or less across a pH range between about 2 and about 8, when in a solution at a concentration of 25 g/L. The term "substantially low turbidity" refers to whey proteins whose physical characteristics are such that they have an NTU of 200 or less across a pH range between about 2 and about 8, when in a solution at a concentration of 25 g/L. The concentration of whey protein in solutions of the invention includes 25 g/L; however, this concentration is not meant to be limiting in any way and is used as a standard for purposes of determining the level of turbidity of a solution. Thus, the standard of 25 g/L is simply the concentration at which the physical properties (i.e., extent of denaturation) of a whey protein isolate are measured. In other words, when the isolated whey proteins are in a solution at that concentration, they have a certain level of turbidity at a certain pH. The level of turbidity for a standardized protein amount on a gram per liter basis can be extrapolated from a measurement using a sample a concentration of 25 g/L. Thus, the turbidity units in the pH ranges discussed above can apply to a concentration of whey proteins that is about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 g/L or more, or any range derivable therein. It is contemplated that turbidity can be measured in NTU, as described herein, such as in the Examples.

It will be understood that a "nondenatured" whey protein or whey protein isolate refers to whey proteins that have an NTU of about 1000 or less across a pH range from about 2 to about 8 (in a solution having 25 g/L of whey protein). It will be understood that a "substantially nondenatured" whey protein or whey protein isolate refers to whey proteins that have an NTU of about 200 or less across a pH range from about 2 to about 8 (in a solution having 25 g/L of whey protein—"standard concentration"). Thus, "nondenatured" whey proteins or a whey protein isolate refers to whey proteins having an NTU of about 1000, 900, 800, 700, 600, 500, 400, 300, 200, or less at the isoelectric points of the whey proteins when at the standard concentration.

Methods of the invention involve employing ion exchange chromatography, particularly cation exchange chromatography because of the chemical properties of whey proteins. Embodiments involve a cation exchange support, which refers to a physical structure containing cation exchangers, that is, having a negatively charged stationary phase. The exchangers may be on or part of a filter or semi-permeable membrane or on a solid structure, such as a particle, bead, paddle, stirrer, slide, plate, or dish. In particular embodiments, the support is a bead, which may or may not be porous. Methods of the invention involve, in some embodiments, a bead that is not porous. Beads for ion exchange chromatography are readily available, and can be purchased through a number of vendors. The size of the beads can vary, though in particular embodiments, the average diameter of a wet bead is about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500 μm (micrometers) or more, or any range derivable therein. In certain embodiments, the bead size is about 80 μm to about 150 μm in diameter, and in specific embodiments, the bead size is about 100 μm to about 300 μm in diameter.

In certain embodiments, a charged support is a gel or resin or part of a gel or resin. Beads can be contained in such mixtures. Gels or resins may be contained in a non-reacting structure, which refers to a physical structure that holds the charged item(s). It is contemplated that the physical structure may be a column, such as those readily used in chromatography procedures, as well as a tank or other vessel that could hold the sample and the item on which the ion exchange occurs, such beads or other porous or solid support. In particular embodiments, a column holds beads that provide the support for separating molecules on the basis of charge. Moreover, pre-packed columns are also readily available, such as Amersham Biosciences' Mono S columns. Furthermore, the column diameter can vary. In certain embodiments, the column diameter is about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500 or more cm, or any range derivable therein. However, it is contemplated that large scale production using methods of the invention is possible by scaling up the reactions described herein. Thus, much larger columns, such as on the order of about or at least about 2×, 5×, 10×, 20×, 50×, or 100× larger than the columns described above can be employed. The volume of the structure or support can vary as well. It is contemplated that the volume can be about, at least about, or at most about 1, 5, 10, 15, 20, 25, 30, 35, 40, 45, 50, 55, 60, 65, 70, 75, 80, 85, 90, 95, 100, 200, 300, 400, 500, 600, 700, 800, 900, 1000, 1100, 1200, 1300, 1400, 1500, 1600, 1700, 1800, 1900, 2000, 3000, 4000, 5000, 6000, 7000, 8000, 9000, 10,000, 15,000, 20,000, 25,000 ml or liters or more, or any range derivable therein. The upper volumes are specifically contemplated for large-scale isolation of whey proteins.

In methods of the invention whey proteins are applied to the cation exchange support. It is contemplated that prior to subjecting the whey proteins to ion exchange chromatography, other steps may be implemented towards isolating or purifying whey proteins. Whey proteins can be isolated from any variety of cheese or milk product. It is contemplated that whey proteins may be collected after milk has been pasteurized (in whey), such as during the cheesemaking process, or they may be collected without undergoing the cheesemaking process, such as from microfiltered milk. After whey or whey proteins is collected, in some embodiments of the invention, physical separation means are employed. In particular embodiments, the whey proteins are filtered before applying it to the cation exchange support. Different filtration devices and methods can be employed, including the use of a pleated sheet cartridge filter.

The ion exchange support can be prepared for chromatography using standard methods, such as equilibrating the column prior to applying the sample. Typically, the support is equilibrated with a solution ("equilibration solution") that is similar, such as in pH, to the solution in which the sample is. In embodiments of the invention, the solution comprises a salt and has a pH of about, at least about, or at most about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0 or more, or any range derivable therein.

The whey proteins are applied to the cation exchange support under conditions to promote their adsorption to the support. The term "adsorption" is used according to its plain and ordinary meaning to a protein biochemist. This meaning is understood as "the process by which specific substances in solution adhere to the exposed reactive groups of a solid material with which they are in contact." In certain embodiments of the invention, whey proteins are applied to the support in a solution having a pH of about, at least about, or at most about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0 or more, or any range derivable therein. In certain embodiments, the pH of the solution is between about 1 and about 7, or particularly at about 4 or 4.1.

Moreover, whey proteins can be applied to the support at temperatures of about, at least about, or at most about 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50° C. or more, or any range derivable therein. In specific embodiments, the temperature is between about 10° C. and about 40° C. It is further contemplated that these temperatures may also be applied during other steps during the chromatography, such as the elution or desorption step, or washing steps. Applying the whey proteins to the support may involve passing a solution containing whey proteins multiple times (i.e., more than once) over or onto the support.

After the whey proteins are adsorbed to the ion exchange support, one or more steps can follow. In certain embodiments, a support may be washed with a wash solution. Typically, the wash solution is applied or added to the support to remove substances that are not adsorbed to the support. In embodiments of the invention, the wash solution is the same solution as the equilibration solution and/or adsorption solution. In embodiments of the invention, a support is rinsed with a solution having a pH of about, at least about, or at most about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0 or more, or any range derivable therein. The solution comprises a salt in some embodiments. In other embodiments, a support may be rinsed with water.

In some embodiments, it is contemplated that the equilibration solution, adsorption solution, and/or wash solution do not have a pH that will lead to desorption of the protein from the charged support. Thus, embodiments of the invention involve non-desorption solutions that have a pH at about or below about 7, 6, 5, 4, 3, or 2, or any range derivable therein.

Moreover, these solutions, in addition to a desorption solution, may be buffered. The adsorption solution has a buffer in several embodiments of the invention. It is contemplated that in particular embodiments, the buffer has a pKa above about 4.0. Thus buffers used in methods of the invention are contemplated to have a pKa of about or at least about 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0 or more, or any range derivable therein. For example the buffer may comprise phosphate, glycine, citrate, TRIS, HEPES, TES, carbonate and, imidizole buffers. In certain embodiments of the invention, the buffer is phosphate, citrate, or a combination of both. The concentration of buffer in the solution is about, at least about, or at most about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 21, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900 mM (millimolar) or more, or any range derivable therein. In particular aspects of the invention, the concentration of one or more buffers in the solution totals between about 0.5 mM and about 100 mM, or less than about 20 mM.

The buffer may be added to the solution as a salt. Thus, in some cases, the adsorption solution contains a compound that acts as a salt and buffer, such as sodium phosphate. In certain embodiments, the solution also contains sodium chloride.

In certain embodiments, a solution contains a salt, which is a term used according to its ordinary and plain meaning in chemistry. The term "salt" is understood as referring to a "compound formed by the union of an acid radical with a basic radical." The ionic strength of the solution (0.5 [molality×(valence)$^2$]) or the concentration of salt or salts in the solution may be about, at least about, or at most about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 21, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900 mM (millimolar) or millimolal, or any range derivable therein. In specific embodiments, the concentration of salt in the desorption solution is between about 0.5 mM and about 100 mM, or it may be less than about 20 mM. In embodiments of the invention, the salt includes, but is not limited to, sodium salt; however, other salts such as potassium salt are contemplated for use in solutions.

After the whey proteins are adsorbed, they may be desorbed from the support using a desorption solution. The term "desorption" is used according to its ordinary and plain meaning in the field of protein chemistry to refer to the "liberation of a substance from the support upon which it is adsorbed." As described above, the desorption solution may be buffered, for example with a phosphate and/or citrate system. In some embodiments the desorption solution may comprise multiple buffering agents. In certain embodiments, it contains a salt, as described above. Furthermore, because of the charge on the whey proteins, the desorption solution has a basic pH, or a pH of about or at least about 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, or any range derivable therein, in methods of the invention.

In some embodiments, one or more properties of the desorption solution that flows across the support may be monitored. For example, the protein concentration of the solution may be monitored to determine the amount of protein that is desorbed from the support. In certain embodiments the pH of the solution is monitored before, after, and/or during the time is in contact with the support. In specific embodiments, the pH of the desorption solution coming off the support (exiting solution) is monitored. Thus, in some embodiments the desorbed proteins and buffer may be collected when they reach a certain pH. For example, eluted proteins may be collected when the solution that is or has been incubated with the support reaches a pH of about or at most about 5.0, 5.5, 6.0, 6.5, 7.0, 7.5, 8.0, 8.5, 9.0, 9.5, 10.0, 10.5, 11.0. In some cases the desorbed protein is collected when the solution reaches a pH of about 9.0. In further embodiments of the invention, the desorbed protein solution is pooled and the pH of the eluted protein fraction is determined. In certain embodiments, the total eluted protein solution has a pH of about or less than about 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0. In certain embodiments, the pH of the total eluted protein fraction is about 6.5 or less.

In embodiments of the invention, one or more solutions may be applied in a directional manner to the ion exchange support. It will be understood that applying a solution in a "directional manner" means the solution was applied to the support in a way such that the solution generally moves in one direction across the support. Consequently, in embodiments of the invention, one or more solutions are flowed across the support. For example, when a column is used for chromatography, gravity or a pump or other mechanistic device is used to move the solutions through the column generally in one direction; that is, so the solution flows across the support. The rate at which the desorption solution is applied or flows across or on the support can be rather high. In certain embodiments, the rate is expressed in terms of the volume that the support holds (support volume) as a matter of time. In particular methods of the invention, the desorption solution is applied to the support and/or flowed across the support at a flow rate of about, at least about, or at most about 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 13, 135, 140, 145, 150, 155, 160, 165, 170, 175, 180, 185, 190, 195, 200 support volumes or more per hour, or any range derivable therein. In some embodiments, the flow rate is between about 10 support volumes per hour and about 100 support volumes per hour, between about 50 support volumes per hour and about 90 support volumes per hour, or about 90 support volumes per hour. When the support is a column, the rate may be expressed as "column volumes/hour." The previously adsorbed whey proteins, upon desorption, will be located in the eluate. It will be understood that chromatography conducted under batch-type circumstances (where components are not exchanged) will typically not involve a flow rate but a stirring or other mechanism. In embodiments in which the purification is done in batch, it will be understood that in many cases the desorption solution does not flow in a directional manner, such as when purification is done in a tank and/or the exposure of the desorption solution to the entire support occurs at the same time.

In certain embodiments the pH of the desorption solution may be changed over time as the buffer is passed across the support. For example, the pH of the desorption solution may be raised over time as the desorption buffer is applied to the support. It will be understood to one of skill in the art that as the desorption buffer is applied to the support the pH of the solution will change as it passes across the support, generating a pH front. Therefore, in some embodiments the pH of the desorption buffer may be lowered as it is applied to the support such that the pH value at the front reaches a certain maximal value during the time when the adsorption buffer is applied. For example the pH of the adsorption buffer may be lowered from an initial value such that the maximal pH of the front is about or less than about 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In certain embodiments, changing the pH of the desorption solution may comprise mixing two or more solutions in various ratios prior to their application to the support comprising adsorbed whey protein. In further embodiments, the mixed solutions may comprise different buffering agents, and in some cases the buffering agents my have maximal buffering capacity over different pH ranges.

Following desorption, the desorbed whey protein can be collected and subjected to one or more additional manipulations. In certain embodiments of the invention, the concentration of the desorbed whey proteins is altered. For example, they are subjected to ultrafiltration in some embodiments of the invention. For example the desorbed whey protein may be concentrated to about or greater than about 10, 11, 12, 13, 14, 15, 16, 17, 18, 19, 20, 21, 22, 23, 24, 25, 26, 27, 28, 29, or 30 percent total solids by ultrafiltration. In other embodiments, the desorbed whey protein is dried or lyophilized. The protein can be spray dried in some cases. Moreover, the whey protein isolate may thereafter be dissolved in a solution.

Specific embodiments of the invention include the following methods, and any permutations discussed above. The invention encompasses methods for preparing whey proteins comprising: a) contacting whey proteins to a column under conditions to allow whey proteins to be adsorbed to the column, wherein the column comprises a cation exchange resin or gel having beads with a diameter of at least 100 µM; and, b) flowing a desorption solution across the support, wherein the desorption solution has a pH of about 7 or more. It further involves methods for preparing whey proteins comprising: a) applying whey proteins to a cation exchange column under conditions to allow whey proteins to be adsorbed to the column; and, b) flowing a desorption solution through the column at a flow rate between about 10 column volumes per hour and 200 column volumes per hour, wherein the desorption solution has a pH of about 7 or more. Other methods for preparing whey proteins include: a) applying whey proteins to a cation exchange support under conditions to allow whey proteins to be adsorbed to the support; and, b) flowing a desorption solution across the support, wherein the desorption solution has a buffer, an ionic strength between about 0.5 mM and about 100 mM, and a pH of about 11.5. In particular embodiments, there are methods for preparing substantially nondenatured whey proteins comprising: a) applying whey proteins to a column under conditions to allow whey proteins to be adsorbed to the column, wherein the column comprises a cation exchange resin or gel having beads with a diameter of at least 100 µM; and, b) flowing a desorption solution across the support at a flow rate between about 10 column volumes per hour and 200 column volumes per hour, wherein the desorption solution has a buffer and an ionic strength between about 0.5 mM and about 100 mM and a pH of about 7 or more.

It is also contemplated that specific whey proteins may be selectively desorbed from a charged support. Thus, methods of the invention include separation of one or more specific whey proteins from other components in the whey, including other whey proteins. This can be implemented in a pH-dependent manner. In specific embodiments, α-lactalbumin is first desorbed using a solution having a pH of about 4.9 and the β-lactoglobulin-rich protein fraction is specifically desorbed by using a desorption solution having a pH of about 11.5.

In some embodiments the methods of the invention involve implementing affinity purification of whey proteins in a batch. The term "batch" is used according to its ordinary and plain meaning in this field to refer to a process in which components of the purification process are incubated together, generally without regard to order or direction. In the context of the present invention, it is contemplated that purification in batch does not. In these embodiments of the invention, methods include: a) contacting whey proteins with a cation exchange support under conditions to allow the whey proteins to be adsorbed to the support; b) contacting the support with a desorption solution wherein the desorption solution has a pH of about 7 or more; and, c) collecting the desorbed whey proteins. In some embodiments, the support may be enclosed in a tank, and in certain embodiments the support and solutions may be in motion relative to one another. For example the solution may be stirred or agitated during one or more of the steps of the invented method. In some embodiments of batch purification the pH of the desorption solution and/or the desorbed whey protein solution may be monitored over the course of the purification. Thus, in certain embodiments the pH of the desorption solution and/or the desorbed protein solution may be adjusted. In yet further embodiments of the batch purification method of the invention, the turbidity of the desorption solution and/or the desorbed protein solution maybe monitored over the course of the purification. Embodiments described herein with respect to directional chromatography may be implemented with respect to batch purification, and vice versa.

In addition to process methods for preparing a whey protein isolate, the invention includes compositions that include the whey protein isolate. It is contemplated that solutions and compositions may be potable or used in edible food compositions, or formulation to be pharmacologically or pharmaceutically acceptable. Compositions and solutions include, but are not limited to, food products, such as beverages, dietary supplements, and drugs.

The present invention includes solutions comprising whey proteins, wherein the solution has turbidity characteristics described above when the concentration of whey proteins is at about 25 g/L. In certain embodiments, the solution has a turbidity below about 400 NTU across a pH range of about 2 to about 8. Alternatively, it can have a turbidity below about 200 NTU across that pH range. Even still, the solution may have a turbidity below about 50 NTU. Moreover, in other embodiments solution with 25 g/L of whey protein have a turbidity below about 200 NTU across a pH range of about 4 to about 6, or a turbidity below about 50 NTU across a pH range of about 4 to about 6. In certain embodiments the solution of the invention may have a turbidity at or below about 50 NTU over a pH range of about 6 to about 8. Thus, the whey protein solution may have a turbidity of less than about 40 NTU at a pH of about 7, and/or less than about 50 NTU at a pH of about 6. In some embodiments the protein solution may have a turbidity less than about 150 NTU at a pH range of about 4.5 to about 5.5. Thus, the solution may have a turbidity of less than about 75 NTU at a pH of about 5.5. In still yet a further embodiment of the current invention the whey protein solution has a turbidity of less than about 110 NTU at a pH of about 4.

Certain embodiments of the invention concern compositions comprising whey protein isolate that is substantially soluble over a pH range of about 2 to about 8. Substantially soluble whey protein isolate is defined as conferring a turbidity of less than about 10, 15, 20, 25, 30, 35, 40, 45, 50, 60, 70, 80, 90, 100, 110, 120, 130, 140, 150, 160, 170, 180, 190 or 200 NTU over at a pH of about 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.05.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0 or any range derivable therein, when in solution at a concentration of about 25 g/L. In certain embodiments whey protein isolate of the invention may have a turbidity at or below about 50 NTU over a pH range of about 6 to about 8. Therefore substantially soluble whey protein isolate may a turbidity of less than about 40 NTU at a pH of about 7, and/or less than about 50 NTU at a pH of about 6. In some embodiments the whey protein may have a turbidity less than about 150 NTU at a pH range of about 4.5 to about 5.5. Thus, the solution may have a turbidity of less than about 75 NTU at a pH of about 5.5. In still yet a further embodiment of the current invention the substantially soluble whey protein isolate has a turbidity of less than about 110 NTU at a pH of about 4. In some embodiments of the invention the substantially soluble whey protein isolate may be used in a solutions having a pH of about or at most 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.05.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, or any range derivable therein.

Other embodiments of the invention concern compositions comprising substantially isolated nondenatured whey proteins, either as a whey protein isolate or as individual whey proteins. In addition to the definition of "whey protein isolate" described earlier, it will be understood that the term "substantially isolated" or "substantially purified" means the whey protein(s) is separated away from other undesirable components, which could be other whey proteins, such that the desired protein is in an amount that is about or at least about 80, 81, 82, 83, 84, 85, 86, 87, 88, 89, 90, 91, 92, 93, 94, 95, 96, 97, 98, 99 or more percent, or any range derivable therein, of the total weight of the weight of solids in a sample. Of course, casein, fat or lactose can be added to the compositions comprising substantially isolated whey proteins without altering the understanding of that term. Furthermore, the term "substantially isolated nondenatured" whey proteins refers to whey proteins that are substantially isolated and substantially nondenatured, as defined above.

Because of the clarity that can be achieved with whey protein isolates of the invention, beverages and other foodstuffs having this isolate are contemplated. In some embodiments, there is a high protein clear beverage comprising substantially purified whey protein. A "high protein clear beverage" means a beverage with a protein concentration of at least about 25 g/L, a turbidity of about or less than about 100 NTU across a pH of at least about 4 to about 6. It is contemplated that the beverage has a natural or artificial sweetener, such a sugar, in additional embodiments of the invention. In certain embodiments, the amount of sweetener is about, at least about, or at most about 1, 2, 3, 4, 5, 6, 7, 8, 9, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 350, 400, 450, 500 g/L or more, or any range derivable therein. In particular embodiments, the amount of sugar in the beverage is about 100 g/L. Alternatively, the amount can be expressed as about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 g of sugar per 240 mls of liquid, or any range derivable therein. In particular embodiments, the amount of sugar is 18 grams or less per 240 mls. Moreover, such beverages may be considered as having "reduced sugar" or "reduced calories," according to industry standards. It is specifically contemplated that whey protein isolates of the invention can be used in sports and diet drinks. The pH values for the beverage can be any pH described with respect to whey protein isolates discussed above.

Other embodiments of the invention include, but are not limited to, an edible composition, a food ingredient, a thickening and stabilizing food product such as an infant formula or an enteral formula, an emulsion, a foam, or a pharmaceutical composition. Such compositions may or may not have a low sugar content, such as can be found in foodstuffs known as diet and health foods.

It is contemplated that any method or composition described herein can be implemented with respect to any other method or composition described herein. Moreover, it is clearly contemplated that embodiments may be combined with one another, to they extent they are compatible.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

It is specifically contemplated that any embodiments described in the Examples section are included as an embodiment of the invention.

Following long-standing patent law, the words "a" and "an," when used in conjunction with the word "comprising" in the claims or specification, denotes one or more, unless specifically noted.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-B. Nephelos Turbidity Units (NTU) versus pH of Whey Protein Isolate solutions containing 25 g/L whey protein. Commercial samples (A=ALACEN Whey Protein isolate, NZMP, Lemoyne, Pa., USA, B=BiPRO, Davisco Foods Intl., Eden Prairie, Minn., U.S.A.) were compared to a samples made using the invented product made using the process described above (C=Grande Cheese Co., Brownsville, Wis.). FIG. 1A. Graph showing turbidity profile after elution with 0.01 M sodium phosphate, pH 11.5. FIG. 1B. Graph showing turbidity profile after elution with 0.01 M sodium phosphate and 0.015 sodium chloride, pH 11.5.

FIG. 2. Nephelos Turbidity Units (NTU) versus pH of prototype beverages containing 25 g/L whey protein and 100 g/L sucrose. Commercial samples (A=BiPRO, Davisco Foods Intl., Eden Prairie, Minn., U.S.A. and B=PowerPro, Land O'Lakes Food Ingredients, Arden Hills, Minn., U.S.A.) were compared to a sample made at the University of Wisconsin, Madison, using the proposed process (C=Wisconsin). The shaded region covers the pH range for acid foods as defined by the Food and Drug Administration.

(FIG. 4B) ALACEN 895, NZMP, Lemoyne, Pa., USA, (FIG. 4C), BiPRO, Davisco Foods Intl., Eden Prairie, Minn., U.S.A (FIG. 4D). All samples were equilibrated to 25 g protein per L. Graphs plot Nephelos Turbidity Units (NTU) versus pH of Whey Protein Isolate solutions.

DESCRIPTION OF ILLUSTRATIVE EMBODIMENTS

Figure 3:
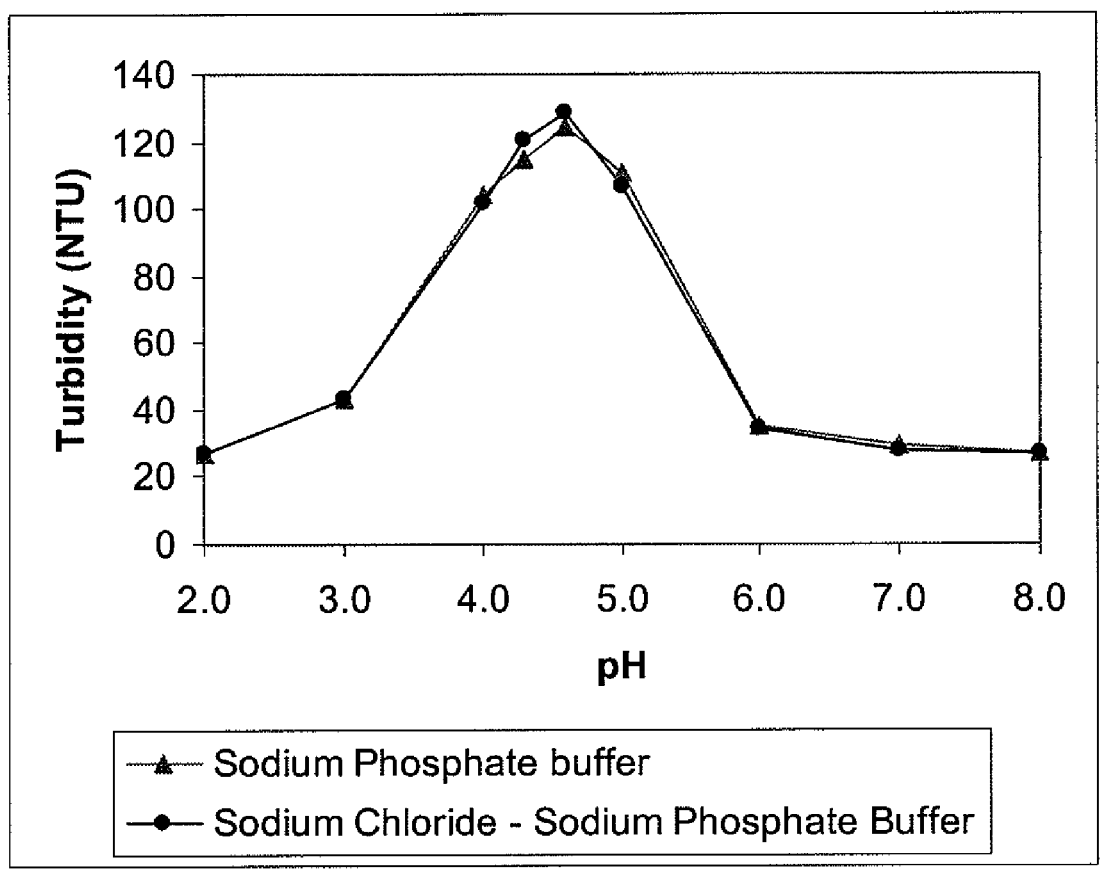
FIG. 3. Proteins were isolated from mozzarella cheese whey and separated by ion exchange chromatography as described herein. Samples were eluted with either 0.01 M sodium phosphate, pH: 11.5 or with 0.01 M sodium phosphate, 0.015M NaCl at pH: 11.5, as indicated. Following elution protein solutions were spray dried and equilibrated to a protein concentration of 25 g/L for turbidity analysis. Graph plots Nephelos Turbidity Units (NTU) versus pH of whey protein isolate solutions that were isolated with the indicated elution buffer.

The present invention concerns methods and compositions that involve whey protein isolates. It provides methods for isolating or purifying whey proteins from a sample in a way that substantially limits or prevents their denaturation across a range of pH values. As a result, the yields from such reactions have a number of applications because the nondenatured whey proteins are substantially pure and they are not aggregated, thus making a solution cloudy or turbid. Methods of the invention generally involving employing ion exchange chromatography in conjunction with a number of improved ways of desorbing whey protein during the chromatography procedure. Such ways concern the physical characteristics of the ion exchange support—including its volume and/or surface area (size of beads)—buffer conditions, and application of buffers and solutions.

I. Whey Proteinaceous Compositions

Whey proteins comprise one of the two major protein groups of bovine milk and account for approximately 20% of the milk composition. However, the present invention is not limited to whey protein from bovine milk and can be implemented with respect to the milk from other species. Whey protein is derived as a natural byproduct of the cheese-making process. In addition to proteins, the raw form contains fat, lactose and other substances. The raw form is processed to produce protein-rich whey protein concentrates (WPC) and whey protein isolates (WPI), among other things. Thus, whey proteins are comprised of high-biological-value proteins and proteins that have different functions. The primary whey proteins are β-lactoglobulin and α-lactalbumin, two small globular proteins that account for about 70 to 80% of total whey protein. Proteins present in lesser amounts include the immunoglobulins IgG, IgA and IgM, but especially IgG, glycomacropeptides, bovine serum albumin, lactoferrin, lactoperoxidase and lysozyme.

Thus, in certain embodiments, the present invention concerns protein compositions comprising at least one proteinaceous molecule, such as a whey protein. Typically, the whey protein is a nonrecombinant protein, that is, the protein is the natural product of a cell. As used herein, a "proteinaceous molecule," "proteinaceous composition," "proteinaceous compound," "proteinaceous chain" or "proteinaceous material" generally refers, but is not limited to, a protein of greater than about 50 amino acids or the full length endogenous sequence translated from a gene; a polypeptide of greater than about 100 amino acids; and/or a peptide of from about 3 to about 100 amino acids. All the "proteinaceous" terms described above may be used interchangeably herein.

In certain embodiments the proteinaceous composition comprises at least one protein, polypeptide or peptide. For example, a whey protein isolate is a proteinaceous composition. In further embodiments the proteinaceous composition comprises a biocompatible protein, polypeptide or peptide. It is contemplated that recombinant or altered whey proteins can be isolated by methods of the invention. The altered whey proteins may possess desirable properties for a variety of applications. These altered proteins may be biocompatible. As used herein, the term "biocompatible" refers to a substance which produces no significant untoward effects when applied to, or administered to, a given organism according to the methods and amounts described herein. Such untoward or undesirable effects are those such as significant toxicity or adverse immunological reactions. In preferred embodiments, biocompatible protein, polypeptide or peptide containing compositions will generally be mammalian proteins or peptides or synthetic proteins or peptides each essentially free from toxins, pathogens and harmful immunogens.

The term "biologically functional equivalent" is well understood in the art and is further defined in detail herein. Accordingly, sequences that have between about 70% and about 80%; or more preferably, between about 81% and about 90%; or even more preferably, between about 91% and about 99%; of amino acids that are identical or functionally equivalent to the amino acids of a whey protein provided the biological activity of the protein is maintained.

II. Isolation and Purification of Whey Proteins

In particular embodiments, the present invention provides a method of preparing or obtaining whey protein from a whey protein-containing sample. This can be accomplished by extracting or isolating the whey protein from the sample. Because of the biochemistry involved in isolating macromolecules such as whey proteins from a sample, the terms "extracting" and "isolating" are used synonymously to refer to the process of separating a whey protein from other components in a whey protein-containing sample. In particular embodiments, the present invention provides an ion exchange method for preparing, obtaining or collecting a whey protein from a whey protein containing sample. In further embodiments, the present invention contemplates a whey protein or whey protein containing sample applied to an ion exchange support and desorbed directionally with a desorption buffer at an appropriate pH. The present invention further contemplates desorbing whey protein directionally to create a moving interface between desorbed whey protein in the mobile phase and absorbed whey protein in the stationary phase such that the desorbed whey protein acts as a buffer.

Typically, purification methods will involve initial methods of cheesemaking and thereafter, curds will be separated from whey proteins. Methods of cheesemaking are well known to those of skill in the art. Such methods include those described in the following patents, which are hereby incorporated by reference: 6,572,901; 6,558,716; 6,551,635; 6,548,089; 6,485,762; 6,475,538; 6,468,570; 6,465,033; 6,458,394; 6,455,092; 6,443,379; 6,416,797; 6,413,568; 6,410,076; 6,401,604; 6,399,121; 6,335,040; 6,297,042; 6,270,823; 6,258,390; 6,242,036; 6,183,804; 6,140,078; 6,139,889; 6,120,809; 6,103,277; 6,026,740; 5,988,052; 5,948,459; 5,853,786; 5,688,542; 5,643,621; 5,635,228; 5,554,398; 5,547,691; 5,505,979; 5,462,755; 5,429,829; 5,395,631; 5,356,639; 5,106,631.

A. Ion Exchange Chromatography

Ion exchange chromatography (IEC) relies on the reversible adsorption-desorption of ions in solution to a charged solid matrix or polymer network. This technique is the most commonly used chromatographic technique for protein separation. In ion exchange chromatography, charged substances are separated via column materials that carry an opposite charge. Three critical steps are employed in ion exchange chromatography: sample application, washing the column to remove weakly bound proteins, and elution of the protein of choice with a properly designed gradient.

The ionic groups of exchanger columns are covalently bound to the gel matrix and are compensated by small concentrations of counter ions, which are present in the buffer. When a sample is added to the column, an exchange with the weakly bound counter ions takes place. Ion exchange chromatography (IEC) is applicable to the separation of almost any type of charged molecule, from large proteins to small nucleotides and amino acids. It is very frequently used for proteins and peptides, under widely varying conditions. However, for amino acids standardized conditions are used.

1. Ion Exchangers and Columns

In ion exchange chromatography two exchanger types are differentiated: basic (positively charged) and acidic (negatively charged). These two types can be further divided into weakly basic or acidic exchangers or strongly basic or acidic exchangers. With strongly basic or acidic materials all functional groups are always present in ionized form vastly independent from the pH value in the specified operating range. For example, the quaternary amino groups ($R_3N^+$—) are positively charged, while the sulfonic acid groups (—$SO_3$—) are negatively loaded. The pK values of the quaternary amino groups are around 14, those of the sulfonate residues below 1.

In addition, weakly basic types (pK values between 8 and 11) and weakly acidic types (between 4 and 6) exist. The weakly basic types consist of secondary and tertiary amino functional groups; the weakly acidic types of carboxyl functional group. Thus, a weakly basic exchanger should only be used at pH values below 8.5, weakly acidic exchangers only at pH values above 6. Outside these ranges strongly basic, or strongly acidic exchangers should be used. Many proteins can be separated as polyanions (pH>pI) or as polycations (pH<pI), as long as the pH stability of the protein of interest allows this selection.

Common functional ion exchanger groups may include, but are not limited to, Trimethylammoniumethyl-group (TMAE-Group), pK>13, strongly basic; Diethylaminoethyl-group (DEAE-Group), pK 11, weakly basic; Dimethylaminoethyl-group (DMAE-Group), pK 8-9, weakly basic; Carboxy-group (COO-Group), pK 4.5, weakly acidic; Sulfoisobutyl-group (SO3-Group), pK<1, strongly acidic; Sulfoethyl-group (SE-Group), pK<1, strongly acidic.

In ion exchange chromatography a positively charged matrix is called an anion-exchanger because it binds negatively charged ions (anions). Anion exchangers can be classified as either weak or strong. The charge group on a weak anion exchanger is a weak base, which becomes deprotonated and, therefore, loses its charge at high pH. DEAE-cellulose is an example of a weak anion exchanger, where the amino group can be positively charged below pH of about 9 and gradually loses its charge at higher pH values. A strong anion exchanger, on the other hand, contains a strong base, which remains positively charged throughout the pH range normally used for ion exchange chromatography (pH 1-14). Anion exchangers provide the best results when the pH value of the buffer is 1.5-2 higher than the pI value of the protein. Lowering the pH value shortens the retention time with anion exchangers. Increasing the ionic strength of the counter ion shortens the retention time (with anion and cation exchangers).

Another type of ion exchanger used in ion exchange chromatography is a cation-exchanger, a negatively charged matrix which binds positively charged ions (cations). Cation exchangers can be classified as either weak or strong. A strong cation exchanger contains a strong acid (such as a sulfopropyl group) that remains charged from pH 1-14; whereas a weak cation exchanger contains a weak acid (such as a carboxymethyl group), which gradually loses its charge as the pH decreases below 4 or 5. Cation exchangers provide the best results when the pH value of the buffer is 1.5-2 units below the protein's pI. Increasing the pH value shortens the retention times with cation exchangers.

Analytical ion exchange columns include strong or weak anion exchangers with the functional group/resin being Quaternary ammonium (QA) and Diethylaminoethyl (DEAE) respectively; and strong or weak cation exchangers with the functional group/resin being Sulfopropyl (SP) and Carboxymethyl (CM) respectively. The columns may be used at a pH ranging from 2-12 and may involve the use of salt concentrations less than 1.5 M.

It is also contemplated in the present invention that a tentacle ion exchanger may be used. With most ion exchange gels the ionic groups (exchangers) are fixed directly on the surface of the matrix. On any given gel matrix, only a certain number of ionic groups can be attached because of the chemistries used and the limited inner surface of the matrix. Once attached, the ionic groups must be accessible to the biopolymers for binding them. The spatial requirements of this binding process dictates the limit in protein binding capacity of these kinds of ion exchangers.

Tentacle ion exchangers, however, covalently anchor the exchanger groups to the matrix via linear polymer chains. Therefore, exchange capacity for proteins can be increased significantly. The medium length of the polymer chains is 15 to 50 monomer units, carrying the same number of side chain ligands. The flexibility of the tentacle allows more accessibility of these sites for the biopolymers because of less steric hindrance. For large proteins, tentacle media provide higher binding capacities compared to conventional supports.

In addition to heat or extreme pH conditions, various surface phenomena on the column matrix can lead to denaturation of proteins and loss of their biologic activity. Denaturations due to conformational changes are often irreversible, but can be prevented or minimized by the use of tentacle ion exchangers, where the backbone of the stationary phase is hidden.

Separation, isolation or extraction of whey protein from a whey protein containing sample may further include using a support such as a column, membrane or slide. Solid supports may include supports involving silica. In some embodiments, the silica is glass. Supports may further include, but are not limited to, columns and filters such as glass fiber filters or columns, cellulose, polymer-based monolithic supports, beads, gels or resins.

Due to the good selectivities and high efficiencies, columns packed with tentacle media provide good chromatographic results and highly concentrated fractions can be obtained. Columns may also be stainless steel columns, acrylic columns or high-density columns with matrices that are silica based, resin based, polymer-based or hydrous oxide based.

Depending on the desired resolution, linear flow rates to 380 cm/hr (=5 ml/min for a 1 cm column) can be used for the S-type gels (strong cation gels). In addition to expressing flow rates as a measure of support volume/hour, flow rates may also be expressed in cm/minute. Using the column in Example 1, about 30 column volumes/hour was about 7.5 cm/min; alternatively, about 150 column volumes was about 375 cm/min. Flow rates in cm/min that correspond to the flow rates described herein as support volume/hr are considered part of the invention. The mechanical stability of the Fractogel® tentacle material allows the use of high flow rates (up to 800 cm/h for M-type gels) without loss of capacity.

2. pH and Selectivity in Ion Exchange Chromatography

The charge on the protein affects its behavior in ion exchange chromatography. Proteins contain many ionizable groups on the side chains of their amino acids as well as their amino—and carboxyl—termini. These include basic groups on the side chains of lysine, arginine and histidine and acidic groups on the side chains or glutamate, aspartate, cysteine and tyrosine. The pH of the solution, the pK of the side chain and the side chain's environment influence the charge on each side chain. In general terms, as the pH of a solution increases, deprotonation of the acidic and basic groups on proteins occur, so that carboxyl groups are converted to carboxylate anions (R—COOH to R—COO—) and ammonium groups are converted to amino groups (R—$NH_3^+$ to R—$NH_2$). In proteins the isoelectric point (pI) is defined as the pH at which a protein has no net charge. When the pH>pI, a protein has a net negative charge and when the pH<pI, a protein has a net positive charge. The pI varies for different proteins.

The property of a protein which govern its adsorption to an ion exchanger is the net surface charge. Since surface charge is the result of weak acidic and basic groups of protein; separation is highly pH dependent. Going from low to high pH values the surface charge of proteins shifts from a positive to a negative charge surface charge. The pH versus net surface curve is an individual property of a protein, and constitutes the basis for selectivity in IEC. At a pH value below its isoelectric point a protein (+surface charge) will adsorb to a cation exchanger (−) such as one containing CM-groups. Above the isoelectric point protein (−surface charge) will adsorb to a anion exchanger (+), e.g. one containing DEAE-groups.

As in all forms of liquid chromatography, conditions are employed that permit the sample components to move through the column with different speeds. At low ionic strengths, all components with affinity for the ion exchanger tightly adsorb at the top of the ion exchanger with nothing remaining in the mobile phase. When the ionic strength of the mobile phase is increased by adding a neutral salt, the salt ions compete with the protein and more of the sample components partially desorb and start moving down the column. Increasing the ionic strength even more causes a larger number of the sample components to be desorbed, and the speed of the movement down the column to increase. The higher the net charge of the protein, the higher the ionic strength needed to bring about desorption. At a certain high level of ionic strength, all the sample components are fully desorbed and move down the column with the same speed as the mobile phase. Somewhere in between total adsorption and total desorption the optimal selectivity for a given pH value of the mobile phase is obtained. Thus, to optimize selectivity in ion exchange chromatography, a pH value is chosen that creates sufficiently large net charge differences among the sample components. Then, an ionic strength is selected that fully utilizes these charge differences by partially desorbing the components. The respective speed of each component down the column is proportional to that fraction of the component which is found in the mobile phase. Thus, the pH of the gradient, elution or sample buffer, or buffer component of the present invention can be between about, about at least, or about at most 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5 or any range therein or greater than. In preferred embodiments, the pH of the desorption buffer/solution is greater than or about 7.0, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, or greater.

3. Buffers

It is necessary to select a resin and buffer so that the protein of interest will bind to the resin. In a cation exchange separation, the protein of interest needs to be positively charged to bind to the stationary phase in the column. It is generally preferred that the buffering ion have the same sign of charge as the ion exchanger used to avoid the changes in pH that may result from adsorption or desorption of the buffering ion when altering the ionic strength. In the context of the present invention, buffers that are contemplated for use with the invention include those with a pKa above about 4.0. This includes phosphate, glycine, citrate, TRIS, TES, Imidizolem succinic, and boric acid, all of which are common biological buffers. In some case lactate glycine is used, or another buffer with a pKa above 4.0.

Positively charged buffering ions are used for anion exchangers and negatively charged ones for cation exchangers. Phosphate buffers are generally used on both anion or cation exchangers. In some embodiments of the invention, the buffer of the invention can further include a salt, which is sodium. The concentration of the buffer is between about, at least about, or at most about 0.1, 0.2, 0.5, 1, 2, 5, 10, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, 2000, 5000 mM or more, or any range therein. The sodium may be provided in the buffer as NaCl. In addition, it may be provided in the buffer in multiple ways, such as by adding more than one compound that includes sodium. All buffers are as pure as possible and may be made up from MilliQ-water and filtered (0.45 or 0.22 μm filter).

Some buffers commonly used in IEC include, but are not limited to, Tris, pH range 7-9, with DEAE ion exchanger; Phosphate, pH range 6-8, with CM (DEAE) ion exchanger; and Acetate, pH range 4-6, with DEAE ion exchanger. Ion exchange containing diethyl aminoethyl (DEAE) or carboxymethyl (CM) groups are most frequently used. Other buffers may include L-histidine at 20 mM with a buffering range of pH 5.5-6.8; bis-Tris at 20 mM with a buffering range of pH 5.8-7.0; bis-Tris propane at 20 mM with a buffering range of pH 6.4-7.3; Triethanolamine at 20 mM with a buffering range of pH 7.3-8.2; or diethanolamine at 20 mM with a buffering range of pH 8.4-9.4 which may all be used for anion exchange chromatography. For cation exchange chromatography the buffers used are acids and may include formate at 20 mM with a buffering range of pH 3.3-4.3; MES at 20 mM with a buffering range of pH 5.5-6.7; acetate at 20 mM with a buffering range of pH 4.2-5.2; phosphate at 20 mM with a buffering range of pH 2.0-7.6; and HEPES at 20 mM with a buffering range of pH 7.6-8.2. Additional buffers may include CHES/TEA or TEAA. The concentration of any of the buffers described herein may vary. The concentration of any of the buffers employed in the present invention may be at about 0, 0.5, 1, 10, 20, 30, 40, 50, 60, 70, 80, 90, 100 mM or greater; or at about 0.2, 0.3, 0.4, 0.5, 0.6, 0.7, 0.8, 0.9, 1.0 M or greater. Moreover, it is contemplated that the specific buffers described above may be modified according to the present invention, such as by reducing the ionic strength and employing it at a lower pH (for adsorbing and washing), such as around 4.0, or at a higher pH (for elution or desorption), such as around 11.5.

Before use, the buffer is thoroughly degassed and passed through a filter, for example, a 1 micron filter. Desorption is then brought about by increasing the salt concentration or by altering the pH of the mobile phase. Alteration of the pH of the mobile phase is discussed elsewhere.

4. Elution Gradient

In order to elute a protein of interest from the column, a gradient such as a salt gradient can be used in ion exchange chromatography. Very often the sample components vary in their adsorption to the ion exchanger such that a single value of the ionic strength cannot make the slow ones pass through the column in a reasonable time. In order to elute these proteins a salt gradient can be used which causes a continuous increase of ionic strength in the mobile phase. The salt concentration may also be varied in buffers/solvents used for IEC so that the more weakly bound proteins will wash off the column in the wash, even if they are positively charged. The salt gradient allows for the sample components to be gradually desorbed in the order of increasing net charge, until all the components are fully desorbed. At this point, however, the components of the sample are already separated. Thus, a salt gradient compresses a chromatogram so as to elute components with widely different adsorptive properties within a reasonable time. If it is necessary to selectively increase resolution somewhere within the gradient, but still to elute the slow components within a reasonable time, a section of lower gradient slope is built into the gradient so that it covers that part of the chromatogram where increased resolution is desired. This is called the adapted gradient technique and requires an advanced programmable gradient device.

Gradient elution plays a role in effecting band broadening. The exchange of sample molecules between the mobile and stationary phases is governed by diffusion, and the band broadening effect operate as the molecules pass through the column. Small particles promote rapid mass transfer, pushing the optimal flow rate towards higher values, and uniform spherical particles minimize the effect of eddy diffusion. In a gradient, the rear of a sample zone moves at a slightly higher speed than the front. This is because the ionic strength of the gradient is slightly higher at the rear. As a consequence, the zone will be sharper than it would be without the gradient. The steeper the gradient, the sharper the zone.

In order to fully utilize the resolving power of a gradient-eluted column, the length of the column is such that it does not exceed that needed to fully desorb the last component. An extra-long column does not produce higher resolution and can result in extra band broadening. In order to achieve optimum results, the gradients used for elution should not be too steep. With a column volume of 4-5 ml (=the content of a 50-10 cartridge), a gradient volume of 20 to 25 ml is sufficient.

B. Batch Purification of Whey Protein

It is contemplated that under certain circumstances, the methods described above may also be applied in a batch method of producing whey protein isolate with high clarity and low protein denaturation. The methods and conditions of batch purification, including pH, temperature, ionic strength and concentration used to equilibrate the resin, promote adsorption, wash the resin and desorb the adsorbed proteins, as described for a column process may also be used in a batch process.

For example a batch purification of the invention may comprise, placing cation-exchange resin in a tank with an equilibration solution and mixing. The equilibration solution may then be drained and a sample solution containing whey proteins placed in the tank and exposed to the resin under conditions that promote protein adsorption to the resin. The conditions promoting adsorption are analogous to those described for the column process. This step may be followed by draining the protein depleted sample solution from the tank and washing the system including the resin with a wash solution as described previously, one or more times. This may then be followed by draining of the wash solution from the tank and exposing the washed resin to conditions that promote desorption on the proteins. This can be achieved by placing the desorption solution in the tank and mixing it with the resin to facilitate desorption of the proteins. As described above, in certain cases the pH of the desorption solution may changed during the course of mixing the solution with the resin. Following desorption, the desorbed whey protein solution may be collected and subjected to one or more additional manipulations as described herein.

C. Purification and Concentration of Whey Protein

Prior to or subsequent to subjecting whey proteins to IEC, they may be subjected to additional purification techniques well known to those of ordinary skill in the art.

Thus, certain aspects of the present invention concern the purification, and in particular embodiments, the substantial purification, of whey protein. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed its activity, as may be assessed, for example, by protein assays, as are known to one of ordinary skill in the art for the specific or desired protein, polypeptide or peptide. These techniques involve, at one level, the crude fractionation of the cellular milieu to certain fractions of different polypeptides.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

Thus, after separated or isolating or extracting the whey protein of the present invention from other proteins or protein components using the ion exchange method disclosed herein, the whey protein may be further purified using chromatographic and electrophoretic techniques to achieve partial or complete purification (or purification to homogeneity). Various techniques suitable for use in protein purification will be well known to those of skill in the art. These include, for example, precipitation with ammonium sulfate, PEG, antibodies and the like or by heat denaturation, followed by centrifugation; chromatography steps such as gel filtration, reverse phase, hydroxylapatite and affinity chromatography; isoelectric focusing; gel electrophoresis; and combinations of such and other techniques. Analytical methods particularly suited to the preparation of a pure whey protein include ultrafiltration, diafiltration, reverse micellar extraction (RM), channel modules, exclusion chromatography; polyacrylamide gel electrophoresis; isoelectric focusing. A particularly efficient method of purifying peptides is fast protein liquid chromatography or even HPLC. Thus, any of a number of protein purification methods known to one of ordinary skill in the art may be used in combination with the ion exchange method of the present invention to obtain or prepare a purified or substantially purified whey protein. As is generally known in the art, it is believed that the order of conducting the various purification steps may be changed, or that certain steps may be omitted, and still result in a suitable method for the preparation of a substantially purified protein or peptide.

Various methods for quantifying the degree of purification of the whey protein would be by any method known to those of skill in the art. An example is found in Method No. 991.20 in Association of Official Analytical Chemists, 2000 Official Methods for Analysis, Vol II, $17^{th}$ Ed. AOAC, Gainthersberg, Md., which is hereby incorporated by reference.

Other methods include, for example, determining the specific activity of an active fraction, or assessing the amount of polypeptides within a fraction by SDS/PAGE analysis. A method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity. As discussed above, a way to describe protein isolation in the field of whey protein production is with respect to the weight of whey protein in a sample as a percentage of the total weight of all solids in the sample.

D. Other Methods of Protein Extraction/Purification

The present invention further contemplates the use of additional methods for extracting or isolating or purifying a whey protein and that may be employed in combination with the ion exchange method of the invention. Such methods may involved the adsorption characteristics of a protein, or size of a protein or charge of a protein.

1. Protein Separation Methods Based on pH a. Affinity Chromatography

Adsorption chromatography involves the separation of compounds by selective adsorption-desorption at a solid matrix that is contained within a column through which the mixture passes. Separation is based on the different affinities of different proteins for the solid matrix. Affinity and ion-exchange chromatography are the two major types of adsorption chromatography commonly used for the separation of proteins. Separation can be carried out using either an open column or high-pressure liquid chromatography.

Affinity chromatography uses a stationary phase that consists of a ligand covalently bound to a solid support. The ligand is a molecule that has a highly specific and unique reversible affinity for a particular protein. The sample to be analyzed is passed through the column and the protein of interest binds to the ligand, whereas the contaminating proteins pass directly through. The protein of interest is then eluted using a buffer solution which favors its desorption from the column. This technique is the most efficient means of separating an individual protein from a mixture of proteins, but it is the most expensive, because of the need to have columns with specific ligands bound to them.

Affinity Chromatography is a chromatographic procedure that relies on the specific affinity between a substance to be isolated and a molecule that it can specifically bind to and is well known in the art. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (e.g., alter pH, ionic strength, and temperature).

b. Protein Separation by Electrophoresis

Electrophoresis relies on differences in the migration of charged molecules in a solution when an electrical field is applied across it. It can be used to separate proteins on the basis of their size, shape or charge.

i. Non-Denaturing Electrophoresis

In non-denaturing electrophoresis, a buffered solution of native proteins is poured onto a porous gel (usually polyacrylamide, starch or agarose) and a voltage is applied across the gel. The proteins move through the gel in a direction that depends on the sign of their charge, and at a rate that depends on the magnitude of the charge, and the friction to their movement:

Proteins may be positively or negatively charged in solution depending on their isoelectric points (pI) and the pH of the solution. A protein is negatively charged if the pH is above the pI, and positively charged if the pH is below the pI. The magnitude of the charge and applied voltage will determine how far proteins migrate in a certain time. The higher the voltage or the greater the charge on the protein the further it will move. The friction of a molecule is a measure of its resistance to movement through the gel and is largely determined by the relationship between the effective size of the molecule, and the size of the pores in the gel. The smaller the size of the molecule, or the larger the size of the pores in the gel, the lower the resistance and therefore the faster a molecule moves through the gel. Gels with different porosity's can be purchased from chemical suppliers, or made up in the laboratory. Smaller pores sizes are obtained by using a higher concentration of cross-linking reagent to form the gel. Gels may be contained between two parallel plates, or in cylindrical tubes. In non-denaturing electrophoresis the native proteins are separated based on a combination of their charge, size and shape.

ii. Isoelectric Focusing Electrophoresis

This technique is a modification of electrophoresis, in which proteins are separated by charge on a gel matrix which has a pH gradient across it. Proteins migrate to the location where the pH equals their isoelectric point and then stop moving because they are no longer charged. This methods has one of the highest resolutions of all techniques used to separate proteins. Gels are available that cover a narrow pH range (2-3 units) or a broad pH range (3-10 units) and one should therefore select a gel which is most suitable for the proteins being separated.

iii. Two Dimensional Electrophoresis

Isoelectric focusing and SDS-PAGE can be used together to improve resolution of complex protein mixtures. Proteins are separated in one direction on the basis of charge using isoelectric focusing, and then in a perpendicular direction on the basis of size using SDS-PAGE.

2. Protein Separation Due to Size Differences

Proteins can also be separated according to their size. Typically, the molecular weights of proteins vary from about 10,000 to 1,000,000 daltons. In practice, separation depends on the Stokes radius of a protein, rather than directly on its molecular weight. The Stokes radius is the average radius that a protein has in solution, and depends on its three dimensional molecular structure. For proteins with the same molecular weight the Stokes radius increases in the following order: compact globular protein<flexible random-coil<rod-like protein.

a. Ultrafiltration

In some embodiments of the present invention, it is contemplated that the desorbed whey protein may be subjected to ultrafiltration. Using this method, a solution of protein is placed in a cell containing a semipermeable membrane, and pressure is applied. Smaller molecules pass through the membrane, whereas the larger molecules remain in the solution. The separation principle of this technique is therefore similar to dialysis, but because pressure is applied separation is much quicker. Semipermeable membranes with cutoff points between about 1,000 to 100,000 are available. That portion of the solution which is retained by the cell (large molecules) is called the retentate, whilst that part which passes through the membrane (small molecules) forms part of the ultrafiltrate. Ultrafiltration can be used to concentrate a protein solution, remove salts, exchange buffers or fractionate proteins on the basis of their size.

b. Dialysis

Dialysis is used to separate molecules in solution by use of semipermeable membranes that permit the passage of molecules smaller than a certain size through, but prevent the passing of larger molecules. A protein solution is placed in dialysis tubing which is sealed and placed into a large volume of water or buffer which is slowly stirred. Low molecular weight solutes flow through the bag, but the large molecular weight protein molecules remain in the bag. Dialysis is a relatively slow method, taking up to 12 hours to be completed. It is therefore most frequently used in the laboratory. Dialysis is often used to remove salt from protein solutions after they have been separated by salting-out, and to change buffers.

C. Size Exclusion Chromatography

This technique, sometimes known as gel filtration, also separates proteins according to their size. A protein solution is poured into a column which is packed with porous beads made of a cross-linked polymeric material (such as dextran or agarose). Molecules larger than the pores in the beads are excluded, and move quickly through the column, whereas the movement of molecules which enter the pores is retarded. Thus molecules are eluted off the column in order of decreasing size. Beads of different average pore size are available for separating proteins of different molecular weights. Manufacturers of these beads provide information about the molecular weight range that they are most suitable for separating. Molecular weights of unknown proteins can be determined by comparing their elution volumes Vo, with those determined using proteins of known molecular weight: a plot of elution volume versus log (molecular weight) should give a straight line. One problem with this method is that the molecular weight is not directly related to the Stokes radius for different shaped proteins.

3. Other Methodology

Reverse micellar extraction (RM) methods offer the potential for continuous extraction of specific proteins from an aqueous mixture, achieving simultaneous concentration and purification of specific proteins in an efficient manner. The RM solvent contains small droplets of water, stabilized within an organic solvent by a surfactant. Because protein molecules often move from an original water phase into these small encapsulated water droplets, RM extraction is an attractive approach for separating proteins from an aqueous solution.

III. Assessing Turbidity of Whey Protein Compositions

The present invention embodies a whey protein product, obtained or prepared or collected by the methods disclosed herein that possesses low to no turbidity in aqueous solution over a wide range of pH, than whey protein concentrates or isolates obtained by other methods. The clarity may also be different at a given pH. Some control over the clarity characteristics of the protein product may be exercised by varying the conditions used in the ion-exchange isolation process as discussed herein. This characteristic of the whey protein product of the invention to form clear solutions is of considerable importance for use in food products such as in edible foodstuffs including drinks, gels, and health products requiring bio-active, nondenatured whey protein.

Thus, the present invention provides a method of measuring or assessing the turbidity and/or haze of a whey protein in a solution. The most commonly used turbidity unit is NTU, or nephelometric turbidity units. Nephelometers are calibrated using standards containing formazin which is a polymer which is similar to milk in appearance. Nephelometers measure scattered light at a 90-degree angle to the axis of the incident light. Haze and turbidity are measured by the nephelometer as turbidity in FTU (Formazin Turbidity Units) and these FTU, in turn, are proportional to particle concentration. Haze can be measured using an instrument that employs a "forward scatter" technique. Instead of placing the scattered light detector at a 90-degree angle to the axis of the incident light, it places the detector at a smaller angle (10-25 degrees) from the axis. The forward scatter measurement is intended to be more sensitive to larger particles.

Another method of turbidity measuring for a protein solution is measuring absorbance using a spectrophotometer at a wavelength somewhere in the range of 400 to 600 nm. Wavelengths of 400, 500 and 600 nm are commonly used. See Zhu and Damodaran (1994), Heat-induced conformational changes in whey protein isolate and its relation to foaming properties, which is hereby incorporated by reference.

Basic information regarding turbidity is described in "Determination of Turbidity," found on the World Wide Web at chemie.uni-lueneburg.de/wtw/turb_e.pdf, which is hereby incorporated by reference.

V. Characteristics and Uses of Whey Protein

Cost-effective, large-scale techniques for concentrating and purifying whey protein products from milk are beneficial to the dairy, food, pharmaceutical and nutraceutical industries. Moreover, the present invention provides a whey protein isolate that is soluble across a range of pHs, which is a particularly desirable property for commercial products.

A. Nutritional Uses and Functional Properties

Nutritionally, whey proteins are complete, high-quality proteins that are in dairy foods (e.g., cows milk), that provide the body with all of the essential amino acids required. Whey proteins are also rich in the branched-chain amino acids leucine, isoleucine and valine, which are important for muscle growth and repair. The short chains and peptides that comprise whey protein make it available for absorption into the body (i.e., at least or at about within ten minutes of ingestion). Some whey proteins may be digested to peptides that may be absorbed and may have various activities (bioactive peptides). Other whey proteins (e.g., bovine serum albumin, beta-lactoglobulin) may yield glutamylcysteine during their digestion, which may be absorbed and serve as a precursor to glutathione in some tissues.

Functionally, whey proteins are highly soluble over a wide pH range and contribute emulsification or solubility, water-binding, thickening or viscosity, foaming, gelation and film-forming properties to food and beverage systems. Whey proteins are also used in wellness foods for their energy-enhancing, muscle-building, immune system-boosting properties.

Whey proteins are also very bland in flavor, making them easy to incorporate into both neutral and low pH dairy beverages, as well as dairy foods. There is no need to mask any off flavors in the whey protein formulations of the present invention as none develop as a result of the ion exchange methods employed for isolating or extracting or preparing the whey protein.

The two primary components of whey, beta-LG and alpha-LB, have desirable functional properties when used as food ingredients, including the ability to stabilize food emulsions as foams and to create protein-based gels for confections, soups, and sauces to name a few potential applications.

Whey proteins are also valuable for their utility within pharmaceutical products. There is interest in creating oral formulations in place of other methods of drug delivery, such as inhalants or through skin patch delivery. The proteins can help pharmaceutical developers create micro-emulsions, by lending greater stability to drugs or by enhancing the solubility and even the absorption of these drugs.

B. Food Products

The present invention provides a whey protein that is clear in suspensions over a wide pH range and has a bland flavor or is non-distasteful. Whey protein isolates contain more than 90% protein on a dry weight basis with negligible amounts of fat, lactose and minerals. The low levels of fat and lactose in whey proteins make them ideal ingredients for formulating sugar-free, low-fat or fat-free dairy foods. Whey proteins are an excellent ingredient for protein fortification of foods such as puddings, bakery products, confections, extruded snacks and oatmeal; and beverages such as dry powdered beverages, ready-to-drink beverages, infant formulas, enteral formulas. Whey protein may also be combined with soy protein isolate to make a low-carbohydrate, high-protein sweet snack foods.

Baked applications may include, but are not limited to, nutrition or protein bars, chocolate chip cookies and peanut butter cookies. The whey protein may also function to bind water in the bars and baked goods, which maintains a soft texture over time. The foaming ability of whey protein is an asset in the production of confections like nougat or whipped products, particularly when used in combination with a stabilizer.

Whey proteins, such as a whey protein of the present invention may be utilized in various application for its film-forming properties, for example, spearmint-flavored breath films have been developed using whey proteins. Whey proteins make excellent oxygen, aroma and oil barrier films at low-to-intermediate relative humidity. The mechanical properties of whey protein films adequately provide durability when used as coatings on food products such as low-moisture food products vulnerable to oxidation or aroma loss in conjunction with a simple, moisture-barrier packaging film bag or films separating layers of homogeneous foods. Whey proteins may also be used as respiration-reducing coatings for fresh fruits and vegetables during storage and transportation; and as oil-barrier films or coatings separating oil-rich ingredients (e.g., nuts) from other components of heterogeneous foods. Whey proteins may also be used for structure-enhancing coatings on friable products such as freeze-dried foods and breakfast cereals; and as gloss coating on chocolate and other confections.

C. Health Uses for Whey Proteins

It is indicated in the art that whey proteins may have antimicrobial, antioxidant, immunomodulatory, and/or anticancer activity. Whey proteins contain components such as glycomacropeptide, as well as the anti-bacterial lactoperoxidase and the anti-microbial, anti-inflammatory, immune system-boosting fraction lactoferrin. Thus, the present invention contemplates the use of the whey protein obtained, prepared or collected by the methods described herein for treating or preventing conditions or disease due to microbes, inflammation, or cancer, but is not limited to such.

Lactoferrin is known to bind very tightly to iron, a nutrient essential to support microbial growth, especially the growth of pathogenic bacteria. Lactoferrin may also inhibit the adsorption and/or penetration of bacteria and viruses in the intestinal wall. Lactoperoxidase may inactivate or kill microorganisms via an enzymatic activity producing reactive oxygen species. Whey proteins are rich in L-cysteine and L-glutamate, two amino acids that are precursors to the tripeptide glutathione. Whey proteins are also abundant in the dipeptide sequence of glutamylcysteine. This dipeptide is also a precursor to glutathione. There is some indication that intake of whey proteins enhance monocyte glutathione levels. Enhanced glutathione levels may also contribute to a possible immunomodulatory role of whey proteins, as well as to the possible antioxidant activity of these proteins.

Whey proteins have been used as the sole proteins in some infant formulas, and has been reportedly to result in fewer allergies in infants. Whey protein in infant formulas may significantly reduced atopic disease in infants as well as reduce the incidence to cow's milk protein sensitivity. Whey proteins may also be used to reduce eczema and diarrhea of non-infectious origin in infants. Thus, it is contemplated that the whey protein of the present invention may be employed in preparing infant formulas.

Whey proteins of the present invention may be employed for treating, reducing, or preventing cancer in a subject by reducing tumor burden, tumor regression, or stabilizating tumor growth. Cancers contemplated in the present invention may include but are not limited to malignant or metastatic cancers such as colon cancer. Whey proteins of the present invention may be employed in combination with an anticancer agent such as a cancer therapeutic agent, or radiotherapeutic agent commonly used for treating cancers.

Whey protein has played an critical role in helping the more than 50 million U.S. adults suffering from hypertension, an independent risk factor for cardiovascular disease. ACE inhibitors prevent Angiotensin Converting Enzyme (ACE) from converting Angiotensin I into Angiotensin II, which causes high blood pressure. Certain hydrolysis processes have been shown to release angiotensin converting enzyme (ACE), inhibitory substances from whey protein. It is suggested that these bioactive peptides inhibit the ACE enzyme from catalyzing the process that causes hypertension, thereby lowering blood pressure. Thus, whey proteins of the present invention may be used for treating, preventing, or reducing hypertension in a subject. Whey proteins of the present invention may also be used in combination with other therapeutic agents for treating hypertension such as but not limited to, antihypertensive agents such a calcium channel blockers.

Whey protein of the present invention may also be employed for building muscle tissue by providing the body with the necessary building blocks to produce amino acids required. Whey protein is found to contain the perfect combination of overall amino acid makeup and in the right concentrations for optimal performance in the body. Importantly, consistent whey protein intake coupled with exercise can result in consistent muscle building. Thus, whey proteins of the present invention may play a role in increasing lean muscle mass, decreasing body fat and providing muscles the fuel they need to recover from strenuous activities, in addition to many other body and health benefits. Such benefits may be provided to a subject orally in the form of a tablet, capsule or pill, or in the form of a food product containing a whey protein of the present invention. In other instances the whey protein of the present invention may be provided to a subject, such as a mammal, by inhalation, intravenously, microprojectile bombardment, but is not limited to such methods of providing or administering, and may be by any method know to one of ordinary skill in the art.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Mozzarella cheese whey (Grande Cheese Co., Brownsville, Wis.) was collected after the cream separator and filtered through a 3 μm pleated sheet cartridge filter. The whey was then adjusted to pH 4.0 using 20% $H_2SO_4$ solution.

An ion exchange column with 10 cm diameter (BPG 100, Amersham Pharmacia Biotech Inc., Piscataway, N.J., USA) packed with 2.38 Liters of 100 μm beaded polystyrene/divinyl benzene cation exchange resin substituted with methyl sulphonate (Mono-S, Amersham Pharmacia Biotech Inc., Piscataway, N.J., USA) connected to a programmable operating system (BioProcess Engineering system, Amersham Pharmacia Biotech Inc., Piscataway, N.J., USA) was used for conducting the ion-exchange part of the experiments. During this part, the clean ion-exchange column was first equilibrated using 0.01 M sodium lactate, pH 4.0. Then 6 column volumes (14.26 L) of the whey at pH 4.0 were passed through the column to facilitate the binding of proteins from the whey onto the resin. Unbound whey constituents were then rinsed from the column using 0.01 M sodium lactate, pH 4.0. The bound proteins were then recovered by elution with 0.01 M sodium phosphate, pH 11.5 (FIG. 1A, line C) or with 0.01 M sodium phosphate, 0.015 M sodium chloride, pH 11.5 (FIG. 1B, line C). Finally the column was rinsed with water. The flow rate was maintained at 90 column volumes (214 L)/hr through all these ion-exchange steps. Ion-exchange was conducted at 10 to 15° C. Deionized water was used for rinsing the column and preparing the buffers.

The eluate solution was concentrated to 10-30% total solids by ultrafiltration using a 10 kDa spiral wound polysulphone membrane at 20° C. and then spray dried in a co-current single stage dryer (Feed pressure 10,000-15000 kPa, Inlet temp=180-185° C., Outlet temp=87-90° C. and Product temp=18-20° C.).

The powdered product was analyzed for total protein and moisture content by standard Kjeldahl's method and the gravimetric method, respectively. It was also analyzed for turbidity as a measure of the comparative level of protein denaturation at different pH and then the results were compared with that of WPI powders made using different methods by different manufacturers. Samples of the spray dried whey protein isolates manufactured using different methods were dissolved in deionized water to make the protein concentration 25 g/L. Turbidity of these samples at different pH values: 2.0, 3.0, 4.0, 4.3, 4.6, 5.0, 6.0, 7.0 and 8.0 was measured as Nephelos Turbidity Units (NTU) using a turbidimeter (Model 966, Orbeco-Hellige, Orbeco Analytical Systems, Inc., Farmingdale, N.Y.). To adjust the pH of the WPI solutions 0.1 N and 1.0 N HCl and 0.1 N and 1.0 N NaOH were used. Any sample that passed the target pH value during pH adjustment was discarded and not considered.

Results

The spray dried WPI samples contained 92.5 to 93% total proteins and 5-6% moisture. The results of the turbidity measurements are shown in FIG. 1A-B. Product C in both FIG. 1A and FIG. 1B, the whey protein product of this invention, had lower turbidity than the other commercial whey protein isolates (A and B in FIG. 1), especially in the pH range of about 4.0 to 5.5. This result indicates that the whey proteins in product C are less denatured than those in the other products tested (Damodaran 1996). The performance of WPI products made using elution buffer 0.01 M sodium phosphate, pH 11.5 (FIG. 1A) and with 0.01 M sodium phosphate, 0.015 M sodium chloride, pH 11.5 (FIG. 1B) were almost identical during the turbidity measurements. But there was ~15-20% less buffer required to elute the same amount of proteins when 0.015M NaCl was present in the buffer.

Example 2

Materials and Methods

Mozzarella cheese whey (Grande Cheese Co., Brownsville, Wis.) was collected after the cream separator and filtered through a 3 μm pleated sheet cartridge filter. The whey was then adjusted to pH 4.0 using 20% $H_2SO_4$ solution and passed through a single S-type cation exchange column. Bound proteins were rinsed free of lactose and minerals using 0.01 M sodium lactate, pH 4.0, and desorbed using 0.01 M sodium phosphate, 0.15 M sodium chloride, pH 11.0 buffer until the effluent reached pH 9.0. This solution was concentrated by ultrafiltration at 20° C. Prototype clear beverage compositions were manufactured by adjusting the protein and sucrose concentration to 25 g and 100 g per Liter, respectively. For comparison beverages were also manufactured using protein isolate from two other commercial sources (Bi-PRO, Davisco Foods Intl., Eden Prairie, Minn., U.S.A. and B=PowerPro, Land O'Lakes Food Ingredients, Arden Hills, Minn., U.S.A.), as indicated. Turbidity of these beverages was measured at different pH values (FIG. 2).

Results

The protein beverage solution of the invention (FIG. 2, line C) meets the target for a clear (NTU<50) high-protein beverage containing 25 g protein and 100 g of sucrose per Liter over a wide pH range. Aqueous solutions prepared using proteins obtained from whey by other methods failed to meet this target (FIG. 2, lines A and B).

Example 3

Materials and Methods

Mozzarella cheese whey (Grande Cheese Co., Brownsville, Wis.) was collected after the cream separator and filtered through a 3 μm pleated sheet cartridge filter. The whey was then adjusted to pH 4.0 using 20% $H_2SO_4$ solution.

An ion exchange column with 10 cm diameter (BPG 100, Amersham Pharmacia Biotech Inc., Piscataway, N.J., USA) packed with 2.38 Liters of 100 μm beaded polystyrene/divinyl benzene cation exchange resin substituted with methyl sulphonate (Mono-S, Amersham Pharmacia Biotech Inc., Piscataway, N.J., USA) connected to a programmable operating system (BioProcess Engineering system, Amersham Pharmacia Biotech Inc., Piscataway, N.J., USA) was used for conducting the ion-exchange part of the experiments. During this part, the clean ion-exchange column was first equilibrated using 0.01 M sodium lactate, pH 4.0. Then 6 column volumes (14.26 L) of the whey at pH 4.0 were passed through the column to facilitate the binding of proteins from the whey onto the resin. Unbound whey constituents were then rinsed from the column using 0.01 M sodium lactate, pH 4.0. The bound proteins were then recovered by elution with 0.01 M sodium phosphate, pH 11.5 or with 0.01 M sodium phosphate, 0.015 M sodium chloride, pH 11.5 (FIG. 1). Finally the column was rinsed with water. The flow rate was maintained at 90 column volumes (214 L)/hr through all these ion-exchange steps. Ion-exchange was conducted at 10 to 15° C. Deionized water was used for rinsing the column and preparing the buffers.

The eluate solution was concentrated to 10-12% total solids by ultrafiltration using a 10 kDa spiral wound polysulphone membrane at 20° C. and then spray dried in a co-current single stage dryer (Feed pressure 10,000-15000 kPa, Inlet temp=180-185° C., Outlet temp=87-90° C. and Product temp=18-20° C.).

The powdered product was analyzed for total protein and moisture content by standard Kjeldahl's method and the gravimetric method, respectively. It was also analyzed for turbidity as a measure of the comparative level of protein denaturation at different pH and then the results were compared with that of WPI powders made using different methods by different manufacturers, listed in Table 1. Samples of the spray dried whey protein isolates manufactured using different methods were dissolved in deionized water to make the protein concentration 25 g/L. Turbidity of these samples at different pH values: 2.0, 3.0, 4.0, 4.3, 4.6, 5.0, 6.0, 7.0 and 8.0 was measured as Nephelos Turbidity Units (NTU) using a turbidimeter (Model 966, Orbeco-Hellige, Orbeco Analytical Systems, Inc., Farmingdale, N.Y.). To adjust the pH of the WPI solutions 0.1 N and 1.0 N HCl and 0.1 N and 1.0 N NaOH were used. Any sample that passed the target pH value during pH adjustment was discarded and not considered.
Results The performance of WPI products made using elution buffer 0.01 M sodium phosphate, pH 11.5 and with 0.01 M sodium phosphate, 0.015 M sodium chloride, pH 11.5 (FIG. 3) were almost identical during the turbidity measurements. But there was ~15-20% less buffer required to elute the same amount of proteins when 0.015M NaCl was present in the buffer.

Figure 4:
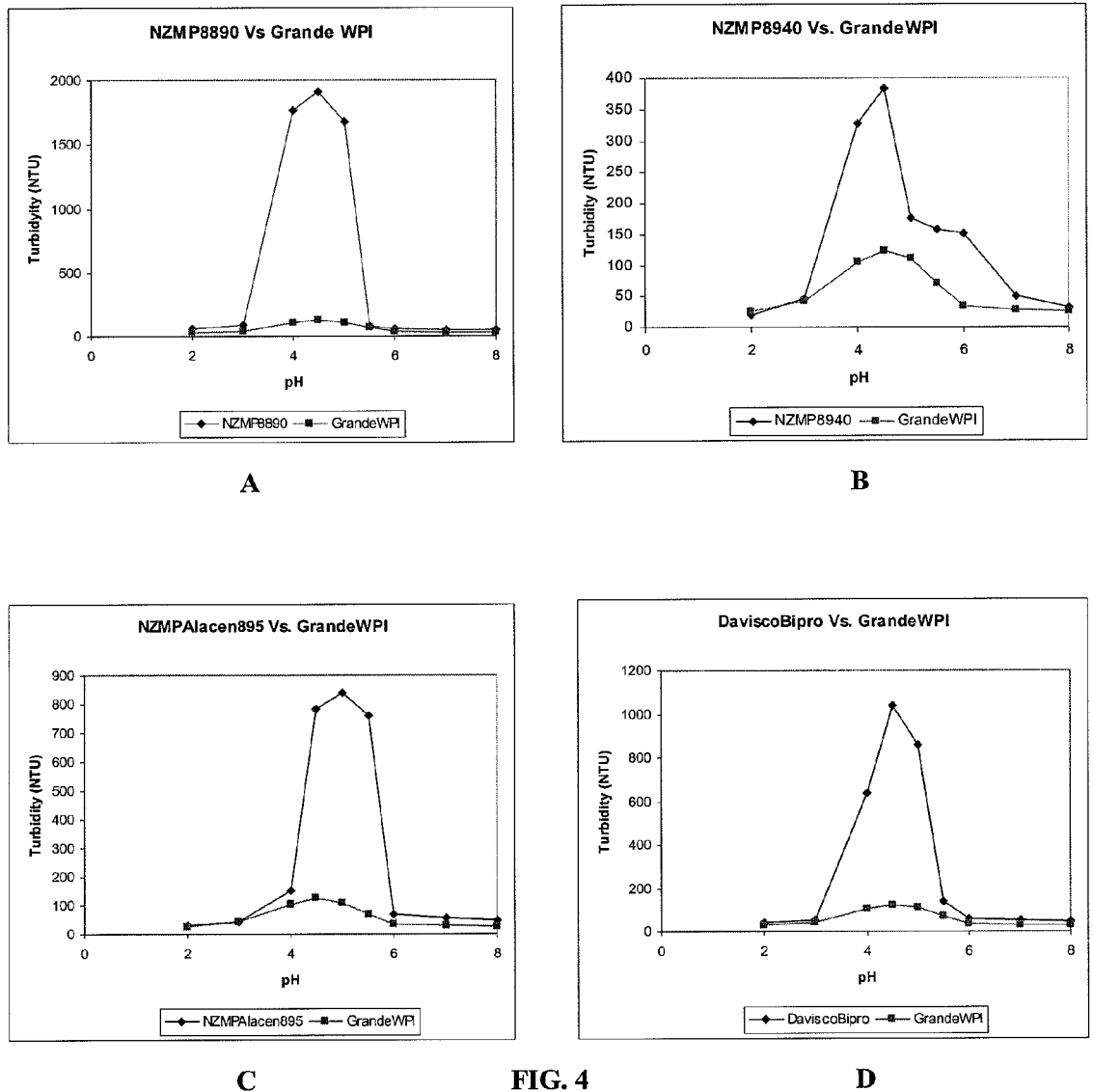
FIGS. 4A-D. A comparison of whey protein isolates from; NZMP 8890, NZMP, Lemoyne, Pa., USA (FIG. 4.A), NZMP 89400, NZMP, Lemoyne, Pa.
Figure 5:
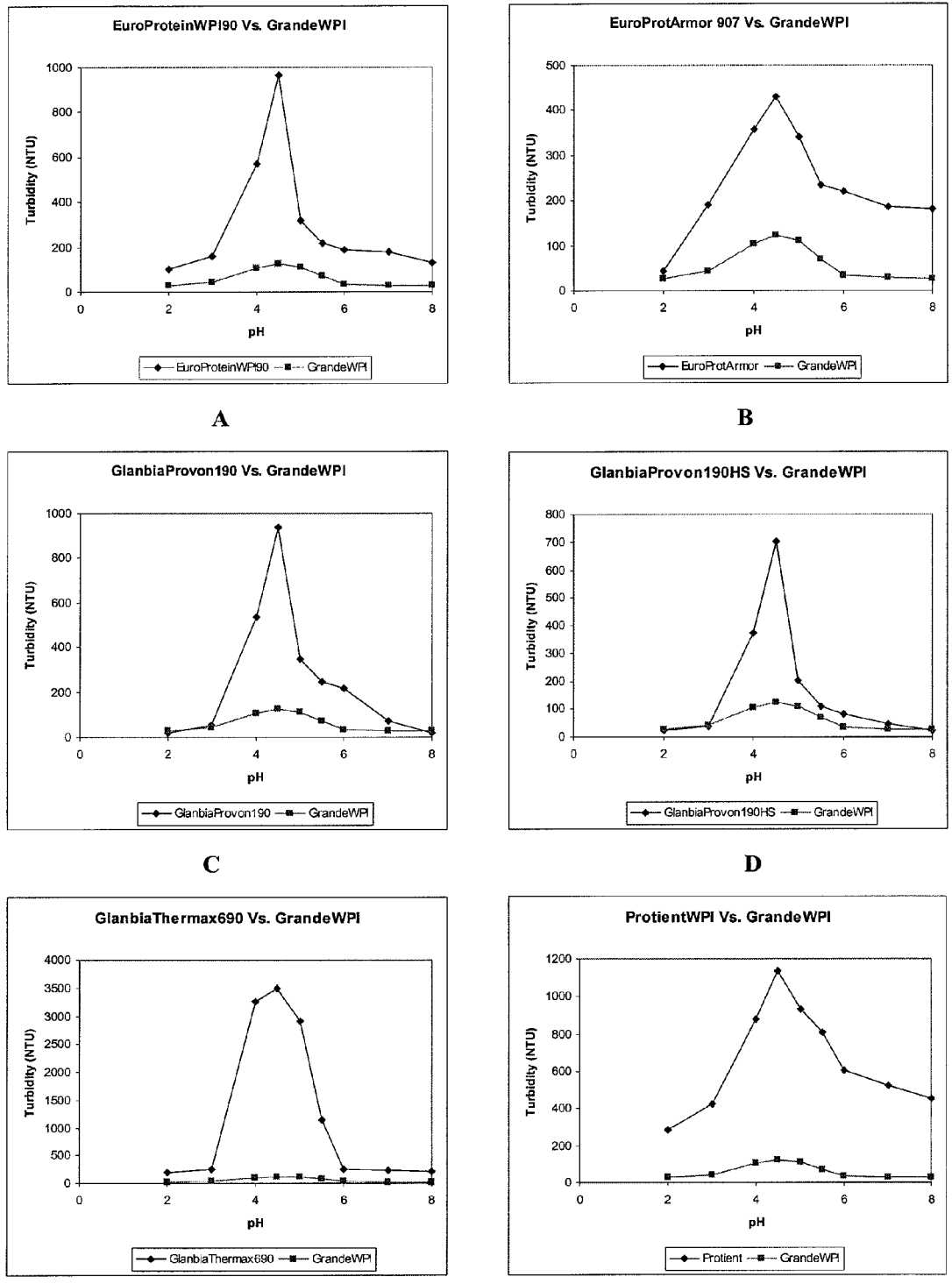
FIGS. 5A-F A comparison of whey protein isolates from; Europrotein WPI 90, Euro Proteins, Wapakoneta, Ohio, USA (FIG. 5A), EuroProtArmor, Euro Proteins, Wapakoneta, Ohio, USA (FIG. 5B), Provon 190, Glanbia Nutritionals, Monroe, Wis., USA (FIG. 5C), Provon 190 HS, Glanbia Nutritionals, Monroe, Wis., USA (FIG. 5D), Thermax 690, Glanbia Nutritionals, Monroe, Wis., USA (FIG. 5E) and Proteient WPI, Protient, St. Paul, Minn., USA (FIG. 5F). All samples were equilibrated to 25 g protein per L. Graphs plot Nephelos Turbidity Units (NTU) versus pH of Whey Protein Isolate solutions.

Both whey protein isolates shown in FIG. 3, had lower turbidity than the other commercial whey protein isolates (Table 1, and FIGS. 4 and 5), and the low turbidity was maintained over a much wider range of pH values than other commercial products. These differences were especially evident in the pH range of about 4.0 to 5.5. This result indicates that the whey proteins in the composition of the invention are less denatured than those in the other products tested (Damodaran 1996).

Sepharose Big Beads cation exchanger (Amersham Biosciences). The bed height of the column was 17 cm to hold 5.34 L of cation exchanger. Flow rate was 2.5 L/min. All buffers were applied into the column at 22±2° C. Whey was applied at 4° C.

The column was equilibrated with 20 L of 50 mM sodium lactate, pH 4.0. Whey (30 L) was pumped into the column to capture the whey proteins. Unbound proteins were rinsed from the column using 10 mM sodium lactate, pH 4.0. Bound proteins were eluted from the column using 45 L of 10 mM sodium phosphate, 150 mM sodium chloride, pH 11.0 until the effluent reached pH 9.0. The pooled elution solution was the desired product and was at pH 6.45.

The pooled elution solution was concentrated to 6% total solids by ultrafiltration using a 3 kDA membrane and used to formulate model beverage solutions containing 25 g/L protein, 100 g/L sucrose, and different values of pH. Turbidity was measured in Nephelos Turbidity Units (NTU) using a turbidity meter (Model 966, Orbeco Analytical Systems,

TABLE 1

| | NZMP | | | Davisco BiPRO | Euro Proteins | | Glanbia Nutritionals | | | | |
|---|---|---|---|---|---|---|---|---|---|---|---|
| | | | | | | | Provon | | | | |
| | 8890 | 8940 | ALACEN 895 | | EP WPI90 | ProtArmor 907 LS | Provon 190 | 190 HS | Thermax 690 | Protient Protient | Grande GrandeWPI |
| pH 8 | | | | | | | | | | | |
| NTU | 46.57 | 31.57 | 48.47 | 46.63 | 130.47 | 180.30 | 20.39 | 25.07 | 222.33 | 453.33 | 26.80 |
| St. Dev | 0.15 | 0.91 | 1.94 | 0.12 | 1.70 | 2.91 | 0.97 | 1.10 | 1.53 | 5.51 | 0.30 |
| pH 7 | | | | | | | | | | | |
| NTU | 49.30 | 50.90 | 56.70 | 50.77 | 178.67 | 185.63 | 70.30 | 48.10 | 230.67 | 524.33 | 29.03 |
| St. Dev | 0.10 | 0.10 | 1.81 | 0.40 | 0.49 | 2.44 | 2.26 | 5.71 | 0.58 | 6.66 | 1.10 |
| pH 6 | | | | | | | | | | | |
| NTU | 63.03 | 151.10 | 68.57 | 57.23 | 190.73 | 219.67 | 219.00 | 81.30 | 246.00 | 605.00 | 34.90 |
| St. Dev | 2.55 | 0.98 | 2.86 | 0.75 | 0.60 | 2.08 | 14.11 | 2.63 | 4.00 | 4.58 | 1.15 |
| pH 5.5 | | | | | | | | | | | |
| NTU | 77.67 | 157.83 | 762.00 | 138.97 | 215.00 | 234.67 | 247.33 | 108.30 | 1142.00 | 810.33 | 70.27 |
| St. Dev | 0.15 | 1.14 | 10.54 | 0.99 | 4.36 | 2.08 | 4.16 | 2.39 | 7.21 | 7.57 | 1.72 |
| pH 5 | | | | | | | | | | | |
| NTU | 1676.67 | 174.80 | 838.33 | 855.33 | 320.67 | 341.00 | 348.33 | 200.07 | 2914.67 | 934.67 | 110.50 |
| St. Dev | 4.16 | 0.72 | 7.23 | 18.15 | 3.79 | 10.58 | 3.79 | 2.11 | 28.94 | 5.13 | 0.46 |
| pH 4.5 | | | | | | | | | | | |
| NTU | 1912.67 | 384.00 | 781.00 | 1039.67 | 964.00 | 429.67 | 938.00 | 704.33 | 3497.33 | 1133.33 | 124.00 |
| St. Dev | 6.11 | 1.00 | 4.36 | 22.50 | 1.00 | 4.51 | 5.29 | 7.09 | 57.18 | 5.03 | 0.26 |
| pH 4 | | | | | | | | | | | |
| NTU | 1762.67 | 327.33 | 151.00 | 640.00 | 571.67 | 357.00 | 535.00 | 374.67 | 3256.00 | 882.00 | 104.47 |
| St. Dev | 16.17 | 2.52 | 5.06 | 7.21 | 2.08 | 5.57 | 4.58 | 5.03 | 12.00 | 9.17 | 1.45 |
| pH 3 | | | | | | | | | | | |
| NTU | 87.53 | 46.37 | 42.37 | 49.67 | 157.87 | 190.37 | 55.37 | 37.87 | 249.33 | 423.67 | 42.97 |
| St. Dev | 1.40 | 0.06 | 1.24 | 0.40 | 2.50 | 1.91 | 3.26 | 2.66 | 1.53 | 5.03 | 0.85 |
| pH 2 | | | | | | | | | | | |
| NTU | 59.10 | 20.03 | 30.40 | 42.73 | 101.37 | 42.47 | 20.83 | 22.80 | 193.57 | 287.33 | 27.20 |
| St. Dev | 0.26 | 1.20 | 2.33 | 1.45 | 1.07 | 1.25 | 0.21 | 0.95 | 1.56 | 3.79 | 0.30 |

Example 4

Figure 6:
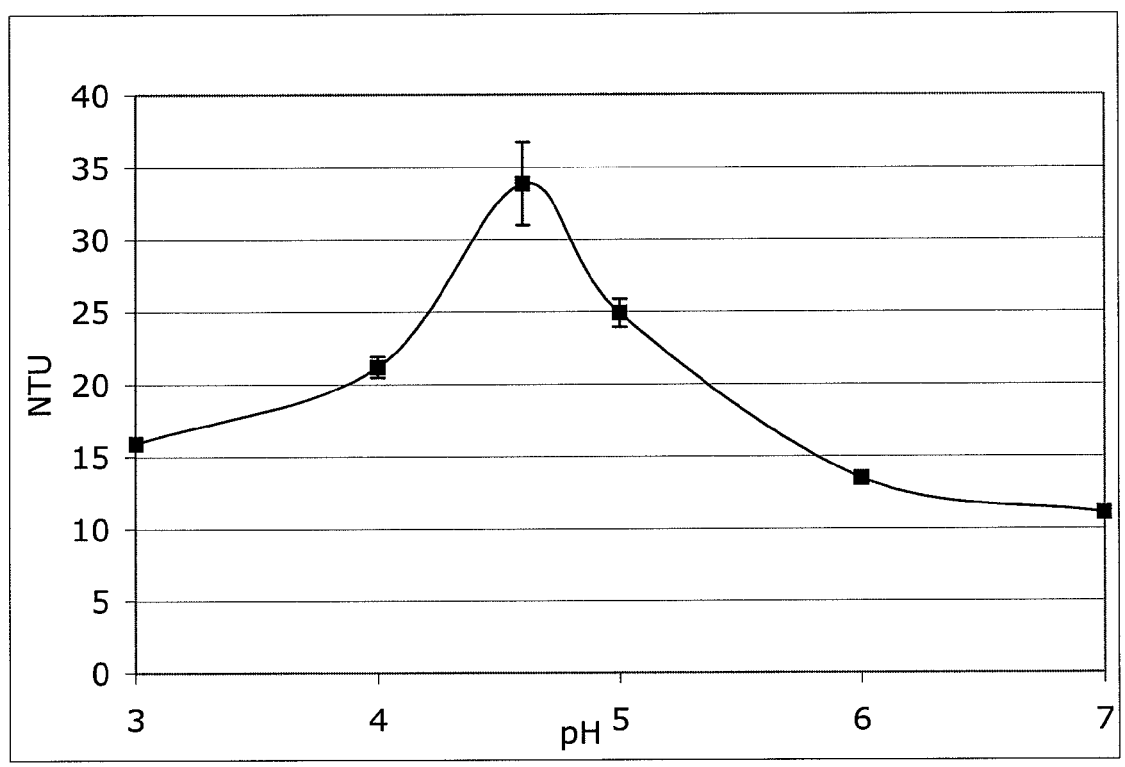
FIG. 6. Nephelos Turbidity Units (NTU) versus pH of prototype beverages containing 25 g/L whey protein and 100 g/L sucrose. Whey protein isolate of the invention was used to manufacture a prototype clear beverage and the turbidity of the beverage was determined over a range of pH from 3 to 7. Error bars indicate standard deviation from the mean.

Mozzarella cheese whey (Grande Cheese Co., Brownsville, Wis., U.S.A) was adjusted to pH 4.0 using 1 M $H_2SO_4$ and filtered using a 3 μm pore size filter ((Sartopure PP2 Capsule, Sartorius Corp., Edgewood, N.Y., U.S.A.) prior to application to the chromatography column. An IndEX 200 chromatography column (20 cm diameter, Amersham Biosciences, Piscataway, N.J., U.S.A.) was packed with SP Farmingdale, N.Y., U.S.A.) (FIG. 6). All solutions were visually clear (NTU<50) at all values of pH. The low turbidity indicates a lack of damage to the proteins manufactured using the method of the invention.

Example 5

The utility of the proposed method to prevent damage to the proteins by preventing exposure to high pH was investigated. The elution solution from Example 4 was adjusted to high pH for either 10 min or 60 min to simulate the exposure to high pH that occurs in commercial manufacturing processes. This solution contained 25 g/L protein and 100 g/L sucrose. After exposure to high pH, the solution was adjusted to pH 4.6, at which turbidity is highest, and the turbidity was measured. Measurement at this pH 4.6 was found to be the most sensitive test of protein damage.

Figure 7:
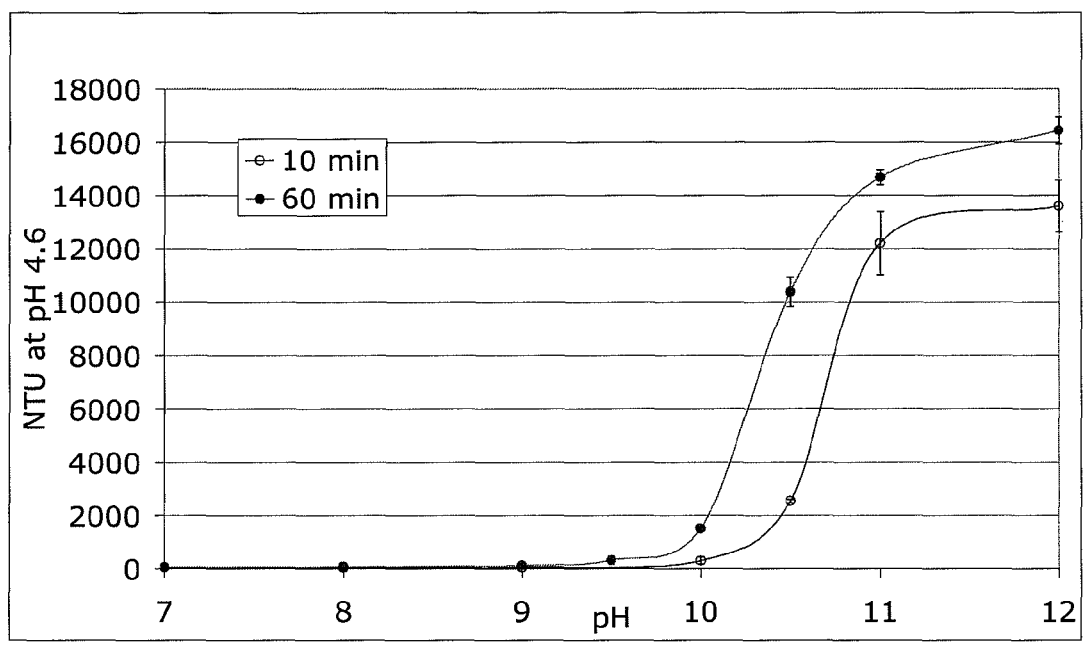
FIG. 7. Solutions containing whey protein isolate of the invention (25 g/L) and 100 g/L of sucrose, were exposed to high pH for 10 or 60 minutes as indicated in FIG. 7. The solution was then adjusted to pH 4.6 and the turbidity (NTU) was measured. Data is plotted as turbidity at pH 4.6 (y-axis) versus the exposure pH (x-axis). Error bars at each data point indicate standard deviation for the mean.

Turbidity increased dramatically after exposure to high pH (FIG. 7). Turbidity increased by 360-fold after exposure to pH 11.0 for 10 min, and 430-fold after exposure to pH 11.0 for 60 min. The comparison was made to a turbidity of 34±3 NTU at pH 4.6 without exposure to high pH (control sample). Conversely, exposure to lower pH did not significantly increase turbidity. Turbidity was 35±2 NTU after exposure to pH 7.0 for 10 min.

Exposure to pH 9.0 for 10 min increased turbidity by only 1.3-fold. Note however that the pooled elution solution was at pH 6.45, and was never exposed to high pH even though the elution solution was at pH 11.0. This is due to flow of the elution solution across the support, which allows the pH to drop as soon as the elution solution contacts the protein adsorbed to the support due to the buffering action of the protein. This allows the use of high pH for elution without exposing the protein to the damage of exposure to high pH.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 5,948,459
U.S. Pat. No. 6,465,033
U.S. Pat. No. 5,106,631
U.S. Pat. No. 5,356,639
U.S. Pat. No. 5,395,631
U.S. Pat. No. 5,429,829
U.S. Pat. No. 5,462,755
U.S. Pat. No. 5,505,979
U.S. Pat. No. 5,547,691
U.S. Pat. No. 5,554,398
U.S. Pat. No. 5,635,228
U.S. Pat. No. 5,643,621
U.S. Pat. No. 5,688,542
U.S. Pat. No. 5,853,786
U.S. Pat. No. 5,988,052
U.S. Pat. No. 6,026,740
U.S. Pat. No. 6,103,277
U.S. Pat. No. 6,120,809
U.S. Pat. No. 6,139,889
U.S. Pat. No. 6,140,078
U.S. Pat. No. 6,183,804
U.S. Pat. No. 6,242,036
U.S. Pat. No. 6,258,390
U.S. Pat. No. 6,270,823
U.S. Pat. No. 6,297,042
U.S. Pat. No. 6,335,040
U.S. Pat. No. 6,399,121
U.S. Pat. No. 6,401,604
U.S. Pat. No. 6,410,076
U.S. Pat. No. 6,413,568
U.S. Pat. No. 6,416,797
U.S. Pat. No. 6,443,379
U.S. Pat. No. 6,455,092
U.S. Pat. No. 6,458,394
U.S. Pat. No. 6,468,570
U.S. Pat. No. 6,475,538
U.S. Pat. No. 6,485,762
U.S. Pat. No. 6,548,089
U.S. Pat. No. 6,551,635
U.S. Pat. No. 6,558,716
U.S. Pat. No. 6,572,901
Association of Official Analytical Chemists, Method No. 991.20, Official Methods for Analysis, Vol II, 17th Ed. AOAC, Gainthersberg, Md., 2000.
Damodaran, In: *Food Chemistry*, Fennema (Ed.), Marcel Dekker Inc., NY, 321-430, 1996.
Etzel, In: *Proceedings of Dry Milk and Whey Technology Forum*: Dairy Management Inc., 44-60, 1998.
Etzel, *J. Nutr.*, 134:996 S-1002S, 2004.
Hambling et al., In *Advanced Dairy Chemistry*, Volume 1 Proteins, Fox (Ed.), Blackie Academic & Professional, N.Y., 141-190, 1997.
Zhu and Damodaran, *J. Agric. Food Chem.*, 42:846-855, 1994.

What is claimed is:

1. A method for preparing nondenatured whey proteins comprising:
   a) contacting whey proteins to a cation exchange support under conditions to allow whey proteins to be adsorbed to the support;
   b) directionally flowing a buffered desorption solution having a pH of more than 9.5 across the support to desorb adsorbed whey proteins and to form a moving interface between desorbed whey proteins in a mobile phase and remaining adsorbed whey proteins, wherein the desorbed whey proteins are nondenatured; and
   c) collecting the desorbed nondenatured whey proteins, wherein the buffered desorption solution that contacts the support is more than pH 9.5.

2. The method of claim 1, wherein the buffered desorption solution has a pH between 9.5 and about 13.

3. The method of claim 2, wherein the buffered desorption solution has a pH of about 11.5.

4. The method of claim 1, wherein the support is on a bead or a membrane.

5. The method of claim 4, wherein the support is on a bead.

6. The method of claim 5, wherein the bead is in a resin or gel.

7. The method of claim 6, wherein the resin or gel is in a non-reacting structure.

8. The method of claim 7, wherein the non-reacting structure is a column.

9. The method of claim 5, wherein the beads have a diameter between about 30 μm and about 500 μm.

10. The method of claim 9, wherein the beads have a diameter between about 100 μm and about 300 μm.

11. The method of claim 1, wherein the buffer is selected from the group consisting of phosphate and citrate.

12. The method of claim 11, wherein the buffer is phosphate.

13. The method of claim 1, wherein the concentration of buffer in the buffered desorption solution is between about 0.5 mM and about 100 mM.

14. The method of claim 13, wherein the concentration of buffer in the buffered desorption solution is less than about 20 mM.

15. The method of claim 1, wherein the buffered desorption solution comprises salt.

16. The method of claim 15, wherein the salt is a sodium salt.

17. The method of claim 16, wherein the sodium salt is sodium phosphate.

18. The method of claim 17, wherein the buffered desorption solution further comprises sodium chloride.

19. The method of claim 1, wherein the buffered desorption solution flows across the support at a flow rate between about 10 support volumes per hour and about 200 support volumes per hour.

20. The method of claim 19, wherein the flow rate is between about 50 support volumes per hour and about 150 support volumes per hour.

21. The method of claim 1, wherein whey proteins are in a solution having a pH between about 1 and about 7 when contacted with the support.

22. The method of claim 21, wherein whey proteins are in a solution having a pH between about 4 and 7 when contacted with the support.

23. The method of claim 1, further comprising subjecting the desorbed whey proteins to ultrafiltration.

24. The method of claim 1, further comprising drying the desorbed whey proteins.

25. The method of claim 24, wherein desorbed whey proteins is spray dried.

26. The method of claim 1, wherein the desorbed whey proteins have a turbidity below about 400 NTU across a pH range between about 2 and about 8 when in a solution comprising 25 mg/ml of desorbed whey proteins.

27. The method of claim 26, wherein the desorbed whey proteins have a turbidity below about 200 NTU across a pH range between about 2 and about 8 when in a solution comprising 25 mg/ml of desorbed whey proteins.

28. The method of claim 27, wherein the desorbed whey proteins have a turbidity below about 100 NTU across a pH range between about 2 and about 8 when in a solution comprising 25 mg/ml of desorbed whey proteins.

\* \* \* \* \*